(12) United States Patent
Hill

(10) Patent No.: US 6,180,624 B1
(45) Date of Patent: Jan. 30, 2001

(54) TACHYKININ ANTAGONIST AND AN OPIOID ANALGESIC EFFECTIVE AT TREATING PAIN OR NOCICEPTION

(75) Inventor: Raymond George Hill, Royston (GB)

(73) Assignee: Merck Sharp & Dohme Limited, Hoddesdon (GB)

( * ) Notice: Under 35 U.S.C. 154(b), the term of this patent shall be extended for 0 days.

(21) Appl. No.: 09/257,414

(22) Filed: Feb. 25, 1999

Related U.S. Application Data

(62) Division of application No. 08/849,968, filed as application No. PCT/GB95/02931 on Dec. 15, 1995, now Pat. No. 5,880,132.

(30) Foreign Application Priority Data

Dec. 23, 1994 (GB) .................................. 94626102

(51) Int. Cl.$^7$ ........................ A61K 31/54; A61K 31/535; A61K 31/44
(52) U.S. Cl. .................................. 514/227.5; 514/227.8; 514/230.8; 514/231.2; 514/231.5; 514/235.5; 514/235.8; 514/236.2; 514/236.8; 514/239.5; 514/282
(58) Field of Search .................. 514/282, 227.5, 514/227.8, 230.8, 231.2, 231.5, 235.5, 235.8, 236.2, 236.8, 239.8

(56) References Cited

U.S. PATENT DOCUMENTS 5,891,842  4/1999  Kream .

FOREIGN PATENT DOCUMENTS

| 0 553 280 | 3/1993 | (EP) . |
| 0 577 394 A1 | * 1/1994 | (EP) . |
| 0 615 751 | 9/1994 | (EP) . |

OTHER PUBLICATIONS

Budavari, S. Editor, The Merck Index, p. 988, entry No. 6186, 1989.*

Tattersall, et al., *Neuropharmacology*, 33 (2) pp. 259–260 (Mar. 15, 1994).

Bountra, C. et al., *European Journal of Pharmacology*, 249 (1) R3–R4 (1993).

* cited by examiner

*Primary Examiner*—William R. A. Jarvis
(74) *Attorney, Agent, or Firm*—J. Eric Thies; David L. Rose

(57) ABSTRACT

This invention relates to methods and compositions for treating pain and nociception in a patient by administering a combination of a morpholine or thiomorpholine tachykinin antagonist and an opioid analgesic.

4 Claims, No Drawings

TACHYKININ ANTAGONIST AND AN OPIOID ANALGESIC EFFECTIVE AT TREATING PAIN OR NOCICEPTION

This application is a divisional of Ser. No. 08/849,968, filed Jun. 20, 1997, now U.S. Pat. No. 5,880,132, which claims priority under 35 U.S.C. 371 to PCT/GB95/02931, filed Dec. 15, 1995.

This invention relates to the treatment or prevention of pain or nociception by the administration of a combination of a tachykinin antagonist, in particular an NK-1 receptor antagonist, and an opioid analgesic.

Pain has been defined as the sensory experience perceived by nerve tissue distinct from sensations of touch, pressure, heat and cold. It is often described by sufferers by such terms as bright, dull, aching, pricking, cutting, burning, etc. This range of sensations, as well as the variation in perception of pain by different individuals, renders a precise definition of pain near impossible. Pain as suffering, however, is generally considered to include both the original sensation and the reaction to that sensation. Where pain is "caused" by the stimulation of nociceptive receptors and transmitted over intact neural pathways, this is termed nociceptive pain. Alternatively, pain may be caused by damage to neural structures, often manifesting itself as neural supersensitivity, and is classed as neuropathic pain.

The level of stimulation at which pain is perceived is referred to as the "pain threshold". Where the pain threshold is raised, for instance, by the administration of an analgesic drug, a greater intensity or more prolonged stimulus is required before pain is experienced. Analgesics are a class of pharmaceutical agent which, following administration to a patient in need of such treatment, relieve pain without loss of consciousness. This is in contrast to other pain-relieving drugs, for example, general anaesthetics which obtund pain by producing a hiatus in consciousness, or local anaesthetics which block transmission in peripheral nerve fibres thereby preventing pain.

Tachykinin antagonists have been reported to induce antinociception in animals, which is believed to be analogous to analgesia in man (for review see Maggi et al, *J. Auton. Pharmacol.* (1993) 13, 23–93). In particular, non-peptide NK-1 receptor antagonists have been shown to produce such analgesia, thus, for example, in classical tests of chemo-nociception (phenylbenzoquinone-induced writhing and formalin test) the NK-1 receptor antagonist RP 67,580 produced analgesia with potency comparable to that of morphine (Garret et al, *Proc. Natl. Acad. Sci. USA* (1993) 88, 10208–10212).

The opioid analgesics are a well-established class of analgesic agent. They are also sometimes referred to as opiates although this term should be reserved for chemical relatives of morphine. The term opioid is generally accepted to refer in a generic sense to all drugs, natural or synthestic, with morphine-like actions. The synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonise the analgesic effects of morphine, when given alone it can be a potent analgesic in its own right.

Of all of the opioid analgesics, morphine remains the most widely used and is a suitable archetype compound. Unfortunately, apart from its useful therapeutic properties, morphine also has a number of drawbacks including respiratory depression, decreased gastrointestinal motility (resulting in constipation) and, in some individuals, nausea and vomiting may occur. Another characteristic is the development of tolerance and physical dependence which may limit the clinical use of such compounds. There is therefore a need to develop methods which enable the clinician to use lower doses of opioid analgesics such as morphine, thereby reducing the likelihood of tolerance and dependence, and thus avoiding the major problem of drug withdrawal associated with cessation of administration.

Morphine-induced emesis may be effectively blocked by the administration of a potent, non-peptide NK-1 receptor antagonist (Bountra et al., *Eur. J. Pharmacol.*, (1993) 249, R3–R4). It is therefore surprising to find that other effects of morphine, notably morphine-induced analgesia, are not blocked by an NK-1 receptor antagonist. Thus, treatment with morphine and an NK-1 receptor antagonist relieves pain without reduction of the morphine analgesic activity, and with the added benefit of enabling lower doses of morphine to be used, as well as reducing the likelihood of nausea and vomiting.

The present invention accordingly provides the use of a tachykinin antagonist and an opioid analgesic for the manufacture of a medicament for the treatment or prevention of pain or nociception.

The present invention also provides a method for the treatment or prevention of pain or nociception, which method comprises administration to a patient in need of such treatment an amount of a tachykinin antagonist and an amount of an opioid analgesic such that together they give effective pain relief.

In a further aspect of the present invention, there is provided a pharmaceutical composition comprising a tachykinin antagonist and an opioid analgesic, together with at least one pharmaceutically acceptable carrier or excipient.

It will be appreciated that the tachykinin antagonist and opioid analgesic may be present as a combined preparation for simultaneous, separate or sequential use for the treatment or prevention of pain. Such combined preparations may be, for example, in the form of a twin pack.

In a further or alternative aspect of the present invention, there is therefore provided a product comprising a tachykinin antagonist and an opioid analgesic as a combined preparation for simultaneous, separate or sequential use in the treatment or prevention of pain or nociception.

The compositions of the present invention are useful for the treatment of pain of any eitiology, including acute and chronic pain and any pain with an inflammatory component. Examples of acute pain include, in particular, post-operative pain, migraine, headache and trigeminal neuralgia. Examples of chronic pain include, in particular, pain associated with musculo-skeletal disorders such as rheumatoid arthritis, osteoarthritis, ankylosing spondylitis, seronegative (non-rheumatoid) arthropathies, non-articular rheumatism and peri-articular disorders, and pain associated with cancer, peripheral neuropathy and post-herpetic neuralgia. Examples of pain with an inflammatory component (in addition to some of those described above) include rheumatic pain, dental pain and dysmenorrhoea.

The compositions of the present invention are especially useful for the treatment of pain where the use of an opioid analgesic is generally prescribed. By the use of a combination of a tachykinin antagonist and an opioid analgesic in accordance with the present invention, it is now possible to treat pain with a sub-maximal dose of an opioid analgesic thereby reducing the likelihood of side-effects associated with opioid analgesic usage (e.g. respiratory depression, constipation, nausea and vomiting, and tolerance and dependence and the associated problem of drug withdrawal).

A particularly preferred use for a composition of the present invention is in the treatment or prevention of postoperative pain.

The tachykinin antagonists of use in the present invention may be any tachykinin antagonist known from the art. Preferably, the tachykinin antagonist is an NK-1 or NK-2 receptor antagonist, especially an NK-1 receptor antagonist.

NK-1 receptor antagonists of use in the present invention are described in published European Patent Specification Nos. 0 360 390, 0 394 989, 0 429 366, 0 443 132, 0 482 539, 0 512 902, 0 514 273, 0 514 275, 0 517 589, 0 520 555, 0 522 808, 0 528 495, 0 532 456, 0 533 280, 0 536 817, 0 545 478, 0 577 394, 0 590 152, 0 599 538 and 0 610 793; and in International Patent Specification Nos. 90/05525, 90/05729, 91/09844, 91/18899, 92/01688, 92/06079, 92/12151, 92/15585, 92/20661, 92/20676, 92/21677, 93/00330, 93/00331, 93/01159, 93/01165, 93/01169, 93/01170, 93/06099, 93/09116, 93/10073, 93/14113, 93/18023, 93/19064, 93/21155, 9321181, 93/23380, 93/24465, 94/01402, 94/02461, 94/03429, 94/03445, 94/04494, 94/04496, 94/05625, 94/07843, 94/10165, 94/10167, 94/10168, 94/10170, 94/11368, 94/13639, 94/13663, 94/14767, 94/15903, 94/19320, 94/19323 and 94/20500; and in British Patent Specification Nos. 2 266 529, 2 268 931, 2 269 170, 2 269 590 and 2 271 774.

Further NK-1 receptor antagonists of use in the present invention are described in published European Patent Specification No. 0 634 402; and in International Patent Specification Nos. 92/17449, 95/02595, 95/06645, 95/07886, 95/07908, 95/08549, 95/14017, 95/15311, 95/17382 and 95/18129.

NK-2 receptor antagonists of use in the present invention are described in published European Patent Specification Nos. 0 347 802, 0 428 434, 0 474 561, 0 512 901 and 0 515 240; and in International Patent Specification Nos. 92/19254 and 93/14084.

One class of tachykinin antagonists of use in the present invention is that described in European Patent Specification No. 0 577 394, i.e. compounds of formula (I):

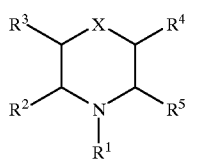

(I)

or a pharmaceutically acceptable salt thereof, wherein:
$R^1$ is selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —NR$^9$R$^{10}$, wherein $R^9$ and $R^{10}$ are independently selected from:
(i) hydrogen,
(ii) $C_{1-6}$alkyl,
(iii) hydroxy-$C_{1-6}$alkyl, and
(iv) phenyl,
(i) —NR$^9$COR$^{10}$, wherein $R^9$ and $R^{10}$ are as defined above,
(j) —NR$^9$CO$_2$R$^{10}$, wherein $R^9$ and $R^{10}$ are as defined above,
(k) —CONR$^9$R$^{10}$, wherein $R^9$ and $R^{10}$ are as defined above,
(l) —COR$^9$, wherein $R^9$ is as defined above,
(m) —CO$_2$R$^9$, wherein $R^9$ is as defined above,
(n) heterocycle, wherein the heterocycle is selected from the group consisting of
(A) benzimidazolyl,
(B) benzofuranyl,
(C) benzthiophenyl,
(D) benzoxazolyl,
(E) furanyl,
(F) imidazolyl,
(G) indolyl,
(H) isoxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1.4-dioxanyl,
(Y) hexahydroazepinyl,
(Z) oxanyl,
(AA) piperazinyl,
(AB) piperidinyl,
(AC) pyrrolidinyl,
(AD) tetrahydrofuranyl, and
(AE) tetrahydrothienyl,
and wherein the heterocylcle is unsubstituted or substituted with one or more substituent(s) selected from:
(i) $C_{1-6}$alkyl, unsubstituted or substituted with halo, —CF$_3$, —OCH$_3$, or phenyl,
(ii) $C_{1-6}$alkoxy,
(iii) oxo,
(iv) hydroxy,
(v) thioxo,
(vi) —SR$^9$, wherein $R^9$ is as defined above,
(vii) halo,
(viii) cyano,
(ix) phenyl,
(x) trifluoromethyl,
(xi) —(CH$_2$)$_m$—NR$^9$R$^{10}$, wherein m is 0, 1 or 2, and $R^9$ and $R^{10}$ are as defined above,
(xii) —NR$^9$COR$^{10}$, wherein $R^9$ and $R^{10}$ are as defined above,
(xiii) —CONR$^9$R$^{10}$, wherein $R^9$ and $R^{10}$ are as defined above,
(xiv) —CO$_2$R$^9$, wherein $R^9$ is as defined above, and (xv) —$(CH_2)_m$—$OR^9$, wherein m and $R^9$ are as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R_9$ is as defined above,
(k) heterocycle, wherein the heterocycle is as defined above;
(4) $C_{2-6}$alkynyl;
(5) phenyl, unsubstitued or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9R^{10}$, wherein m, $R^9$ and $R^{10}$ are as defined above,
(j) —$NR^9COR^{10}$, wherein $R^9$ and $R^{10}$ are as defined above,
(k) —$NR^9CO_2R^{10}$, wherein $R^9$ and $R^{10}$ are as defined above,
(l) —$CONR^9R^{10}$, wherein $R^9$ and $R^{10}$ are as defined above,
(m) —$CO_2NR^9R^{10}$, wherein $R^9$ and $R^{10}$ are as defined above,
(n) —$COR^9$, wherein $R^9$ is as defined above,
(o) —$CO_2R^9$, wherein $R^9$ is as defined above;
$R^2$ and $R^3$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are independently selected from:
(i) —$NR^9COR^{10}$, wherein $R^9$ and $R^{10}$ are as defined above,
(j) —$NR^9CO_2R^{10}$, wherein $R^9$ and $R^{10}$ and as defined above,
(k) —$CONR^9R^{10}$, wherein $R^9$ and $R^{10}$ are as defined above,
(l) —$COR^9$, wherein $R^9$ is as defined above, and
(m) —$CO_2R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$ wherein $R^9$ and $R^{10}$ are as defined above,
(i) —$COR^9$, wherein $R^9$ is as defined above,
(j) —$CO_2R^9$, wherein $R^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9R^{10}$, wherein m, $R^9$ and $R^{10}$ are as defined above,
(j) —$NR^9COR^{10}$, wherein $R^9$ and $R^{10}$ are as defined above,
(k) —$NR^9CO_2R^{10}$, wherein $R^9$ and $R^{10}$ are as defined above,
(l) —$CONR^9R^{10}$, wherein $R^9$ and $R^{10}$ are as defined above,
(m) —$CO_2NR^9R^{10}$, wherein $R^9$ and $R^{10}$ are as defined above,
(n) —$COR^9$, wherein $R^9$ is as defined above,
(o) —$CO_2R^9$, wherein $R^9$ is as defined above;
and the groups $R^1$ and $R^2$ may be joined together to form a heterocyclic ring selected from the group consisting of:
(a) pyrrolidinyl
(b) piperidinyl,
(c) pyrrolyl,
(d) pyridinyl,
(e) imidazolyl,
(f) oxazolyl, and
(g) thiazolyl,
and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;
and the groups $R^2$ and $R^3$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) $C_{1-6}$alkyl,
(ii) $C_{1-6}$alkoxy,
(iii) —$NR^9R^{10}$, wherein $R^9$ and $R^{10}$ are as defined above,
(iv) halo, and
(v) trifluoromethyl;
and the groups $R^2$ and $R^3$ may be joined together to form a heterocyclic ring selected from the group consisting of:

(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl,
and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;
X is selected from the group consisting of:
(1) —O—,
(2) —S—,
(3) —SO—, and
(4) —$SO_2$—;
$R^4$ is selected from the group consisting of:
(1)

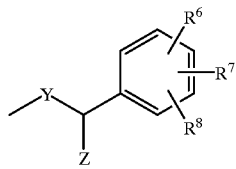

(2) —Y—$C_{1-8}$alkyl, wherein alkyl is unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;
(3) —Y—$C_{2-6}$alkenyl, wherein the alkenyl is unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above,
(4) —O(CO)-phenyl, wherein the phenyl is unsubstituted or substituted with one or more of $R^6$, $R^7$ and $R^8$;
$R^5$ is selected from the group consisting of:
(1) phenyl, unsubstituted or substituted with one or more of $R^{11}$, $R^{12}$ and $R^{13}$;
(2) $C_{1-8}$alkyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9CO^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above;
(4) heterocycle, wherein the heterocycle is as defined above;
$R^6$, $R^7$ and $R^8$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^{10}$ is as defined above, and
(m) —$CO_2R^9$, wherein $R^9$ is as defined above;
(3) $C_{2-6}$alkenyl, unsubstituted or substituted with one or more of the substituent(s) selected from:

(a) hydroxy,
(b) oxo,
(c) $C_{1-6}$alkoxy,
(d) phenyl-$C_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above;
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or $C_{1-5}$alkyl,
(11) —SOR$^{14}$, wherein R$^{14}$ is as defined above,
(12) —SO$_2$R$^{14}$, wherein R$^{14}$ is as defined above,
(13) NR$^9$COR$^{10}$, wherein R$^9$ and R$^{10}$ are as defined above,
(14) CONR$^9$COR$^{10}$, wherein R$^9$ and R$^{10}$ are as defined above,
(15) NR$^9$R$^{10}$, wherein R$^9$ and R$^{10}$ are as defined above,
(16) NR$^9$CO$_2$R$^{10}$, wherein R$^9$ and R$^{10}$ are as defined above,
(17) hydroxy,
(18) $C_{1-6}$alkoxy,
(19) COR$^9$, wherein R$^9$ is as defined above,
(20) CO$_2$R$^9$, wherein R$^9$ is as defined above,
R$^{11}$, R$^{12}$ and R$^{13}$ are independently selected from the definitions of R$^6$, R$^7$ and R$^8$, or —OX;
Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein R$^{15}$ and R$^{16}$ are independently selected from the group consisting of:
(a) $C_{1-6}$alkyl, unsubstituted or substituted with one or more of the substituents selected from:
(i) hydroxy,
(ii) oxo,
(iii) $C_{1-6}$alkoxy,
(iv) phenyl-$C_{1-3}$alkoxy,
(v) phenyl,
(vi) —CN,
(vii) halo,
(viii) —NR$^9$R$^{10}$, wherein R$^9$ and R$^{10}$ are as defined above,
(ix) —NR$^9$COR$^{10}$, wherein R$^9$ and R$^{10}$ are as defined above,
(x) —NR$^9$CO$_2$R$^{10}$, wherein R$^9$ and R$^{10}$ are as defined above,
(xi) —CONR$^9$R$^{10}$, wherein R$^9$ and R$^{10}$ are as defined above,
(xii) —COR$^9$, wherein R$^9$ is as defined above, and
(xiii) —CO$_2$R$^9$, wherein R$^9$ is as defined above;
(b) phenyl, unsubstituted or substituted with one or more of the substituent(s) selected from:
(i) hydroxy,
(ii) $C_{1-6}$alkoxy,
(iii) $C_{1-6}$alkyl,
(iv) $C_{2-5}$alkenyl,
(v) halo,
(vi) —CN,
(vii) —NO$_2$,
(viii) —CF$_3$,
(ix) —(CH$_2$)$_m$—NR$^9$R$^{10}$, wherein m, R$^9$ and R$^{10}$ are as defined above,
(x) —NR$^9$COR$^{10}$, wherein R$^9$ and R$^{10}$ are as defined above,
(xi) —NR$^9$CO$_2$R$^{10}$, wherein R$^9$ and R$^{10}$ are as defined above,
(xii) —CONR$^9$R$^{10}$, wherein R$^9$ and R$^{10}$ are as defined above,
(xiii) —CO$_2$NR$^9$R$^{10}$, wherein R$^9$ and R$^{10}$ are as defined above,
(xiv) —COR$^9$, wherein R$^9$ is as defined above, and
(xv) —CO$_2$R$^9$, wherein R$^9$ is as defined above;
Z is selected from:
(1) hydrogen,
(2) $C_{1-4}$alkyl, and
(3) hydroxy, with the proviso that if Y is —O—, Z is other than hydroxy, or if Y is —CHR$^{15}$—, then Z and R$^{15}$ may be joined together to form a double bond.

A particularly preferred compound of formula (I) is 2-(R)-(1-(R)-(3,5-bis(trifluoromethyl)pheny)lethoxy)-3-(S)-(4-fluorophenyl)4-(3-(5-oxo-1H,4H-1,2,4-triazolo)methyl)morpholine; or a pharmaceutically acceptable salt thereof.

Another class of tachykinin antagonists of use in the present invention are compounds of formula (II):

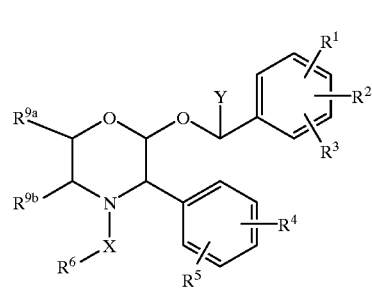

(II)

or a pharmaceutically acceptable salt or prodrug thereof, wherein
R$^1$ is hydrogen, halogen, $C_{1-6}$alkyl, $C_{1-6}$alkoxy, CF$_3$, NO$_2$, CN, SR$^a$, SOR$^a$, SO$_2$R$^a$, CO$_2$R$^a$, CONR$^a$R$^b$, $C_{2-6}$alkenyl, $C_{2-6}$alkynyl or $C_{1-4}$alkyl substituted by $C_{1-4}$alkoxy, where $R^a$ and $R^b$ each independently represent hydrogen or $C_{1-4}$alkyl;

$R^2$ is hydrogen, halogen, $C_{1-6}$alkyl, $C_{1-6}$alkoxy substituted by $C_{1-4}$alkoxy or $CF_3$;

$R^3$ is hydrogen, halogen or $CF_3$;

$R^4$ is hydrogen, halogen, $C_{1-6}$alkyl, $C_{1-6}$alkoxy, $CF_3$, $NO_2$, $CN$, $SR^a$, $SOR^a$, $SO_2R^a$, $CO_2R^a$, $CONR^aR^b$, $C_{2-6}$alkenyl, $C_{2-6}$alkynyl or $C_{1-4}$alkyl substituted by $C_{1-4}$alkoxy, where $R^a$ and $R^b$ each independently represents hydrogen or $C_{1-4}$alkyl;

$R^5$ is hydrogen, halogen, $C_{1-6}$alkyl, $C_{1-4}$alkoxy substituted by $C_{1-4}$alkoxy or $CF_3$;

$R^6$ is a 5-membered or 6-membered heterocyclic ring containing 2 or 3 nitrogen atoms optionally substituted by =O, =S or a $C_{1-4}$alkyl group, and optionally substituted by a group of the formula $ZNR^7R^8$ where Z is $C_{1-6}$alkylene or $C_{3-6}$cycloalkylene;

$R^7$ is hydrogen, $C_{1-4}$alkyl, $C_{3-7}$cycloalkyl or $C_{3-7}$-cycloalkyl$C_{1-4}$alkyl, or $C_{2-4}$alkyl substituted by $C_{1-4}$alkoxy or hydroxyl;

$R^8$ is hydrogen, $C_{1-4}$alkyl, $C_{3-7}$cycloalkyl or $C_{3-7}$cycloalkyl$C_{1-4}$alkyl, or $C_{2-4}$alkyl substituted by one or two substituents selected from $C_{1-4}$alkoxy, hydroxyl or a 4, 5 or 6 membered heteroaliphatic ring containing one or two heteroatoms selected from N, O and S;

or $R^7 R^8$ and the nitrogen atom to which they are attached form a heteroaliphatic ring of 4 to 7 ring atoms, optionally substituted by a hydroxy group, and optionally containing a double bond, which ring may optionally contain an oxygen or sulphur ring atom, a group S(O) or $S(O)_2$ or a second nitrogen atom which will be part of a NH or $NR^c$ moiety where $R^c$ is $C_{1-4}$alkyl optionally substituted by hydroxy or $C_{1-4}$alkoxy;

or $R^7$, $R^8$ and the nitrogen atom to which they are attached form a non-aromatic azabicyclic ring system of 6 to 12 rings atoms;

or Z, $R^7$ and the nitrogen atom to which they are attached form a heteroaliphatic ring of 4 to 7 ring atoms which may optionally contain an oxygen ring atom;

$R^{9a}$ and $R^{9b}$ are each independently hydrogen or $C_{1-4}$alkyl, or $R^{9a}$ and $R^{9b}$ are joined so, together with the carbon atoms to which they are attached, there is formed a $C_{5-7}$ ring;

X is an alkylene chain of 1 to 4 carbon atoms optionally substituted by oxo; and Y is a $C_{1-4}$ alkyl group optionally substituted by a hydroxyl group;

with the proviso that if Y is $C_{1-4}$alkyl, $R^6$ is susbstituted at least by a group of formula $ZNR^7R^8$ as defined above.

A particularly preferred compound of formula (II) is 2-(R)-(1-(R)-(3,5-bis(trifluoromethyl)phenyl)ethoxy)-4-((dimethylaminomethyl)-1,2,3-triazol-4-yl)methyl)-3-(S)-(4-fluorophenyl)morpholine; or a pharmaceutically accpetable salt thereof.

Another class of tachykinin antagonists of use in the present invention are those compounds of formula (III):

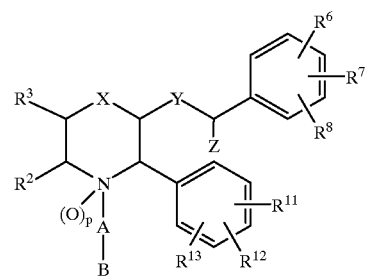

(III)

or a pharmaceutically acceptable salt thereof, wherein:

$R^2$ and $R^3$ are independently selected from the group consisting of:
(1) hydrogen,
(2) $C_{1-6}$alkyl, unsubstituted or substituted with one or more of the substituents selected from:
 (a) hydroxy,
 (b) oxo,
 (c) $C_{1-6}$alkoxy,
 (d) phenyl-$C_{1-3}$alkoxy,
 (e) phenyl,
 (f) —CN,
 (g) halo,
 (h) —$NR^9R^{10}$, wherein $R^9$ and $R^{10}$ are independently selected from:
  (i) hydrogen,
  (ii) $C_{1-6}$alkyl,
  (iii) hydroxy-$C_{1-6}$alkyl, and
  (iv) phenyl,
 (i) —$NR^9COR^{10}$, wherein $R^9$ and $R^{10}$ are as defined above,
 (j) —$NR^9CO_2R^{10}$, wherein $R^9$ and $R^{10}$ are as defined above,
 (k) —$CONR^9R^{10}$, wherein $R^9$ and $R^{10}$ are as defined above,
 (l) —$COR^9$, wherein $R^9$ is as defined above, and
 (m) —$CO_2R^9$, wherein $R^9$ is as defined above;
(3) $C_{2-6}$alkenyl, unsubstituted or substituted with one or more of the substituent(s) selected from:
 (a) hydroxy,
 (b) oxo,
 (c) $C_{1-6}$alkoxy,
 (d) phenyl-$C_{1-3}$alkoxy,
 (e) phenyl,
 (f) —CN,
 (g) halo,
 (h) —$CONR^9R^{10}$ wherein $R^9$ and $R^{10}$ are as defined above,
 (i) —$COR^9$ wherein $R^9$ is as defined above,
 (j) —$CO_2R^9$, wherein $R^9$ is as defined above;
(4) $C_{2-6}$alkynyl;
(5) phenyl, unsubstituted or substituted with one or more of the substituent(s) selected from:
 (a) hydroxy,
 (b) $C_{1-6}$alkoxy,
 (c) $C_{1-6}$alkyl,
 (d) $C_{2-5}$alkenyl,
 (e) halo,
 (f) —CN,
 (g) —$NO_2$,
 (h) —$CF_3$,
 (i) —$(CH_2)_m$—$NR^9R^{10}$ wherein m, $R^9$ and $R^{10}$ are as defined above, (j) —NR$^9$COR$^{10}$, wherein R$^9$ and R$^{10}$ areas defined above,
(k) —NR CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above;

and the groups R$^2$ and R$^3$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) C$_{1-6}$alkyl,
(ii) C$_{1-6}$alkoxy,
(iii) —NR$^9$R$^{10}$, wherein R$^9$ and R$^{10}$ are as defined above,
(iv) halo, and
(v) trifluoromethyl;

and the groups R$^2$ and R$^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl,
and wherein the heterocyclic ring is unsubstituted or substituted with one or more substituent(s) selected from:
(i) C$_{1-6}$alkyl,
(ii) oxo,
(iii) C$_{1-6}$alkoxy,
(iv) —NR$^9$R$^{10}$, wherein R$^9$ and R$^{10}$ are as defined above,
(v) halo, and
(vi) trifluoromethyl;

R$^6$, R$^7$ and R$^8$ are independently selected from the group consisting of:
(1) hydrogen;
(2) C$_{1-6}$alkyl, unsubstituted or substituted with one or more of the substituents selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —CONR$^9$R$^{10}$wherein R$^9$ and R$^{10}$ are as defined above,
(i) —COR$^9$ wherein R$^9$ is as defined above,
(j) —CO$_2$R$^9$, wherein R$^9$ is as defined above;
(4) C$_{2-6}$alkynyl;
(5) phenyl, unsubstituted or substituted with one or more of the substituent(s) selected from:
(a) hydroxy,
(b) C$_{1-6}$alkoxy,
(c) C$_{1-6}$alkyl,
(d) C$_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or C$_{1-5}$alkyl,
(11) —SOR$^{14}$, wherein R$^{14}$ is as defined above,
(12) —SO$_2$R$^{14}$, wherein R$^{14}$ is as defined above,
(13) NR$^9$COR$^{10}$, wherein R$^9$ and R$^{10}$ are as defined above,
(14) CONR$^9$COR$^{10}$, wherein R$^9$ and R$^{10}$ are as defined above,
(15) NR$^9$R$^{10}$, wherein R$^9$and R$^{10}$ are as defined above,
(16) NR$^9$CO$_2$R$^{10}$, wherein R$^9$ and R$^{10}$ are as defined above,
(17) hydroxy,
(18) C$_{1-6}$alkoxy,
(19) COR$^9$, wherein R$^9$ is as defined above,
(20) CO$_2$R$^9$, wherein R$^9$ is as defined above,
(21) 2-pyridyl,
(22) 3-pyridyl,
(23) 4-pyridyl,
(24) 5-tetrazolyl,
(25) 2-oxazolyl, and
(26) 2-thiazolyl;

R$^{11}$, R$^{12}$ and R$^{13}$ are independently selected from the definitions of R$^6$, R$^7$ and R$^8$, or —OX;

A is selected from the group consisting of:
(1) C$_{1-6}$alkyl, unsubstituted or substituted with one or more of the substituents selected from:

(a) hydroxy,
(b) oxo,
(c) $C_{1-6}$alkoxy,
(d) phenyl-$C_{1-3}$alkoxy,
(e) phenyl,
(f) —CN,
(g) halo, wherein halo is fluoro, chloro, bromo or iodo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —CO$_2$R$^9$, wherein R$^9$ is as defined above;
(2) $C_{2-6}$alkenyl, unsubstituted or substituted with one or more of the substituent(s) selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above, and
(j) —CO$_2$R$^9$, wherein R$^9$ is as defined above; and
(3) $C_{2-6}$alkynyl;
B is a heterocycle, wherein the heterocycle is selected from the group consisting of:

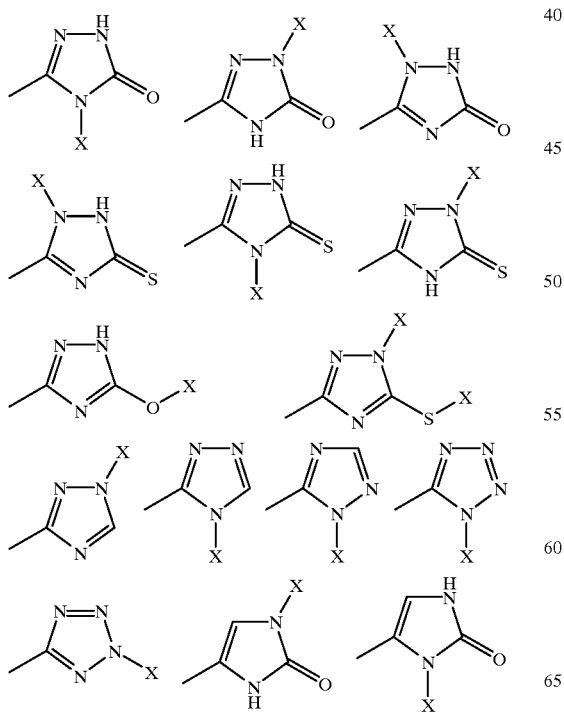

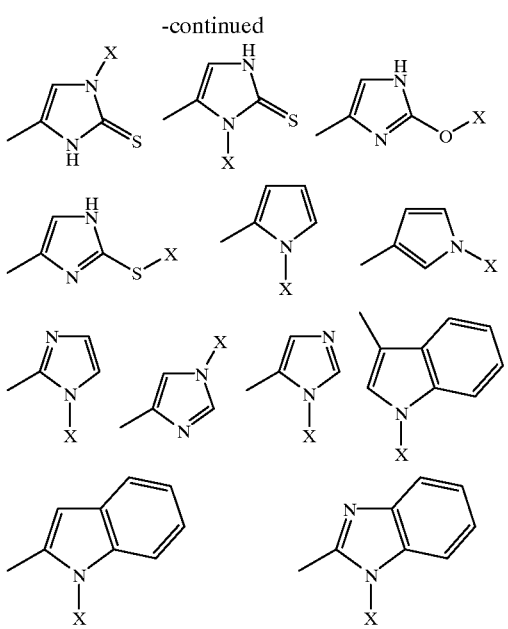

and wherein the heterocycle may be substituted in addition to —X with one or more substituent(s) selected from:
(i) $C_{1-6}$-alkyl, unsubstituted or substituted with halo, —CF$_3$, —OCH$_3$, or phenyl,
(ii) $C_{1-6}$alkoxy,
(iii) oxo,
(iv) hydroxy,
(v) thioxo,
(vi) —SR$^9$, wherein R$^9$ is as defined above,
(vii) halo,
(viii) cyano,
(ix) phenyl,
(x) trifluoromethyl,
(xi) —(CH$_2$)$_m$—NR$^9$R$^{10}$, wherein m is 0, 1 or 2, and R$^9$ and R$^{10}$ are as defined above,
(xii) —NR$^9$COR$^{10}$, wherein R$^9$ and R$^{10}$ are as defined above,
(xiii) —CONR$^9$R$^{10}$, wherein R$^9$ and R$^{10}$ are as defined above,
(xiv) —CO$_2$R$^9$, wherein R$^9$ is as defined above, and
(xv) —(CH$_2$)$_m$—OR$^9$, wherein m and R$^9$ are as defined above;

p is 0 or 1;

X is selected from:
(a) —PO(OH)O$^-$.M$^+$, wherein M$^+$ is a pharmaceutically acceptable monovalent counterion,
(b) —PO(O$^-$)$_2$.2M$^+$,
(c) —PO(O$^-$)$_2$.D$^{2+}$, wherein D$^{2+}$ is a pharmaceutically acceptable divalent counterion,
(d) —CH(R$^4$)—PO(OH)O$^-$.M$^+$, wherein R$^4$ is hydrogen or $C_{1-3}$alkyl,
(e) —CH(R$^4$)—PO(O$^-$)$_2$.2M$^+$,
(f) —CH(R$^4$)—PO(O$^-$)$_2$.D$^{2+}$,
(g) —SO$_3^-$.M$^+$,
(h) —CH(R$^4$)—SO$_3^-$.M$^+$,
(i) —CO—CH$_2$CH$_2$—CO$_2^-$.M$^+$,
(j) —CH(CH$_3$)—O—CO—R$^5$, wherein R$^5$ is selected from the group consisting of:

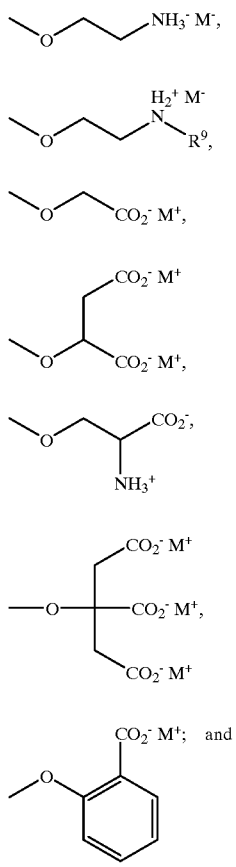

(k) hydrogen, with the proviso that if p is 0 and none of $R^{11}$, $R^{12}$ or $R^{13}$ are —OX, then X is other than hydrogen;

Y is selected from the group consisting of:
(1) a single bond,
(2) —O—,
(3) —S—,
(4) —CO—,
(5) —CH$_2$—,
(6) —CHR$^{15}$—, and
(7) —CR$^{15}$R$^{16}$—, wherein $R^{15}$ and $R^{16}$ are independently selected from the group consisting of:
 (a) C$_{1-6}$alkyl, unsubstituted or substituted with one or more of the substituents selected from:
  (i) hydroxy,
  (ii) oxo,
  (iii) C$_{1-6}$alkoxy,
  (iv) phenyl-C$_{1-3}$alkoxy,
  (v) phenyl,
  (vi) —CN,
  (vii) halo,
  (viii) —NR$^9$R$^{10}$, wherein $R^9$ and $R^{10}$ are as defined above,
  (ix) —NR$^9$COR$^{10}$, wherein $R^9$ and $R^{10}$ are as defined above,
  (x) —NR$^9$CO$_2$R$^{10}$, wherein $R^9$ and $R^{10}$ are as defined above,
  (xi) —CONR$^9$R$^{10}$, wherein $R^9$ and $R^{10}$ are as defined above,
  (xii) —COR$^9$, wherein $R^9$ is as defined above, and
  (xiii) —CO$_2$R$^9$, wherein $R^9$ is as defined above;
 (b) phenyl, unsubstituted or substituted with one or more of the substituent(s) selected from:
  (i) hydroxy,
  (ii) C$_{1-6}$alkoxy,
  (iii) C$_{1-6}$alkyl,
  (iv) C$_{2-5}$alkenyl,
  (v) halo,
  (vi) —CN,
  (vii) —NO$_2$,
  (viii) —CF$_3$,
  (ix) —(CH$_2$)$_m$—NR$^9$R$^{10}$, wherein m, $R^9$ and $R^{10}$ are as defined above,
  (x) —NR$^9$COR$^{10}$, wherein $R^9$ and $R^{10}$ are as defined above,
  (xi) —NR$^9$CO$_2$R$^{10}$, wherein $R^9$ and $R^{10}$ are as defined above,
  (xii) —CONR$^9$R$^{10}$, wherein $R^9$ and $R^{10}$ are as defined above,
  (xiii) —CO$_2$NR$^9$R$^{10}$, wherein $R^9$ and $R^{10}$ are as defined above,
  (xiv) —COR$^9$, wherein $R^9$ is as defined above, and
  (xv) —CO$_2$R$^9$, wherein $R^{10}$ is as defined above;
Z is selected from:
(1) hydrogen,
(2) C$_{1-6}$alkyl, and
(3) hydroxy, with the proviso that if Y is —O—, Z is other than hydroxy, or if Y is —CHR$^{15}$—, then Z and $R^{15}$ may be joined together to form a double bond.

A particularly preferred compound of formula (III) is 2-(R)-(1-(R)-(3,5-bis(trifluoromethyl)phenyl)ethoxy)-3-(S)-(4-fluorophenyl)-4-(3-(4-monophosphoryl-5-oxo-1H, 4H-1,2,4-triazolo)methyl)morpholine; or a pharmaceutically acceptable salt thereof.

Another class of tachykinin antagonists of use in the present invention is that described in European Patent Specification No. 0 436 334, i.e. compounds of formula (IV):

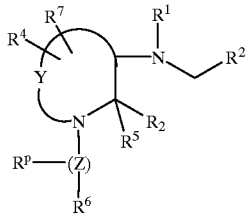

(IV)

or a pharmaceutically acceptable salt thereof, wherein.

Y is (CH$_2$)$_n$ wherein n is an integer from 1 to 4, and wherein any one of the carbon-carbon single bonds in said (CH$_2$)$_n$ may optionally be replaced by a carbon-carbon double bond, and wherein any one of the carbon atoms of said (CH$_2$)$_n$ may optionally be substituted with $R^4$, and wherein any one of the carbon atoms of said (CH$_2$)$_n$ may optionally be substituted with $R^7$;

Z is (CH$_2$)$_m$ wherein m is an integer from 0 to 6, and wherein any one of the carbon-carbon single bonds of (CH$_2$)$_m$ may optionally be replaced by a carbon-carbon double bond or a carbon-carbon triple bond, and any one of the carbon atoms of said (CH$_2$)$_m$ may optionally be substituted with $R^8$;

$R^1$ is hydrogen or C$_{1-8}$alkyl optionally substituted with hydroxy, C$_{1-4}$alkoxy or fluoro;

$R^2$ is a radical selected from hydrogen, C$_{1-6}$ straight or branched alkyl, C$_{3-7}$cycloalkyl wherein one of the CH$_2$ groups in said cycloalkyl may optionally be replaced by NH, oxygen or sulphur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$C_{2-6}$alkyl, benzhydryl and benzyl, wherein each of said aryl and heteroaryl groups and the phenyl moieties of said benzyl, phenyl-$C_{2-6}$alkyl and benzhydryl may optionally be substituted with one or more substituents independently selected from halo, nitro, $C_{1-6}$alkyl, $C_{1-6}$alkoxy, trifluoromethyl, amino, $C_{1-6}$alkylamino, $C_{1-6}$alkyl-O—CO, $C_{1-6}$alkyl-O—CO—$C_{1-6}$alkyl, $C_{1-6}$alkyl-CO—O, $C_{1-6}$alkyl-CO—$C_{1-6}$alkyl-O—, $C_{1-6}$alkyl-CO, $C_{1-6}$alkyl-CO—$C_{1-6}$alkyl-, di-$C_{1-6}$alkylamino, —CONH—$C_{1-6}$alkyl, $C_{1-6}$alkyl-CO—NH—$C_{1-6}$alkyl, —NHCOH and —NHCO—$C_{1-6}$alkyl; and wherein one of the phenyl moieties of said benzhydryl may optionally be replaced by naphthyl, thienyl, furyl or pyridyl;

$R^5$ is hydrogen, phenyl or $C_{1-6}$alkyl;

or $R^2$ and $R^5$ together with the carbon to which they are attached, form a saturated ring having from 3 to 7 carbon atoms wherein one of the $CH_2$ groups in said ring may optionally be replaced by oxygen, NH or sulfur;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of the ($CH_2$) groups in said cycloalkyl may optionally be replaced by NH, oxygen or sulphur;

wherein each of said aryl and heteroaryl groups may optionally be substituted with one or more substituents, and said $C_{3-7}$cycloalkyl may optionally be substituted with one or two substituents, each of said substituents being independently selected from halo, nitro, $C_{1-6}$alkyl, $C_{1-6}$alkoxy, trifluoromethyl, amino, $C_{1-6}$alkylamino, —CO—NH—$C_{1-6}$alkyl, $C_{1-6}$alkyl-CO—NH—$C_{1-6}$alkyl, —NHCOH and —NHCO—$C_{1-6}$alkyl, $R^4$ and $R^7$ are each independently selected from hydroxy, halogen, halo, amino, oxo, cyano, methylene, hydroxymethyl, halomethyl, $C_{1-6}$alkylamino, di-$C_{1-6}$alkylamino, $C_{1-6}$alkyl, $C_{1-6}$alkyl-O—CO, $C_{1-6}$alkyl-O—CO—$C_{1-6}$alkyl, $C_{1-6}$alkyl-CO—O, $C_{1-6}$alkyl-CO—$C_{1-6}$alkyl-O—, $C_{1-6}$alkyl-CO—, $C_{1-6}$alkyl-CO—$C_{1-6}$alkyl, and the radicals set forth in the definition of $R^2$;

$R^6$ is —NHCOR$^9$, —NHCH$_2$R$^9$, SO$_2$R$^8$ or one of the radicals set forth in any of the definitions of $R^2$, $R^4$ and $R^7$;

$R^8$ is oximino (=NOH) or one of the radicals set forth in any of the definitions of $R^2$, $R^4$ and $R^7$;

$R^9$ is $C_{1-6}$alkyl, hydrogen, phenyl or phenyl$C_{1-6}$alkyl; with the proviso that (a) when m is 0, $R^8$ is absent, (b) when $R^4$, $R^6$, $R^7$ or $R^8$ is as defined in $R^2$, it cannot form together with the carbon to which it is attached, a ring with $R^5$, and (c) when $R^4$ and $R^7$ are attached to the same carbon atom, then either each of $R^4$ and $R^7$ is independently selected from hydrogen, fluoro and $C_{1-6}$alkyl, or $R^4$ and $R^7$, together with the carbon to which they are attached, for a $C_{3-6}$saturated carbocyclic ring that forms a spiro compound with the nitrogen-containing ring to which they are attached.

A particularly preferred compound of formula (IV) is (2S,3S)-cis-3-(2-methoxybenzylamino)-2-phenylpiperidine; or a pharmaceutically acceptable salt thereof.

Another class of tachykinin antagonists of use in the present invention is that described in International Patent Specification No. WO 93/21155, i.e. compounds of formula (V):

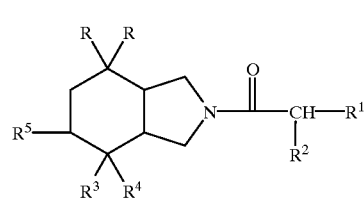

(V)

or a pharmaceutically acceptable salt thereof, wherein radicals R are phenyl radicals optionally 2- or 3-substituted by a halogen atom or a methyl radical;

$R^1$ is optionally substituted phenyl, cyclohexadienyl, naphthyl, indenyl or optionally substituted heterocycle;

$R^2$ is H, halogen, OH, alkyl, aminoalkyl, alkylaminoalkyl, dialkylaminoalkyl, alkyloxy, alkylthio, acyloxy, carboxy, optionally substituted alkyloxycarbonyl, benzyloxycarbonyl, amino or acylamino;

$R^3$ is optionally 2-substituted phenyl;

$R^4$ is OH or fluorine when $R^5$ is H;

or $R^4$ and $R^5$ are OH;

or $R^4$ and $R^5$ together form a bond.

A particularly preferred compound of formula (V) is (3aS, 4S, 7aS)-7,7-diphenyl-4-(2-methoxyphenyl)-2-[(2S)-(2-methoxyphenyl)propionyl]perhydroisoindol-4-ol; or a pharmaceutically acceptable salt thereof.

Another class of tachykinin antagonists of use in the present invention is that described in European Patent Specification No. 0 591 040, i.e. compounds of formula (VI):

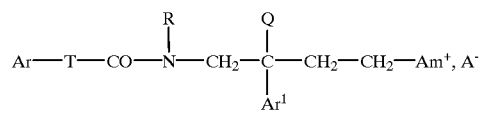

wherein

Ar represents an optionally substituted mono-, di- or tricyclic aromatic or heteroaromatic group;

T represents a bond, a hydroxymethylene group, a $C_{1-4}$alkoxymethylene group or a $C_{1-5}$alkylene group;

Ar' represents a phenyl group which is unsubstituted or substituted by one or more substituents selected from halogen, preferably chlorine or fluorine, trifluoromethyl, $C_{1-4}$alkoxy, $C_{1-4}$alkyl where the said substituents may be the same or different: a thienyl group; a benzothienyl group; a naphthyl group; or an indolyl group;

R represents hydrogen, $C_{1-4}$alkyl, ω-$C_{1-4}$alkoxy$C_{1-4}$alkyl, or ω-$C_{2-4}$alkanoyloxy$C_{2-4}$alkyl;

Q represents hydrogen;

or Q and R together form a 1,2-ethylene, 1,3-propylene or 1,4-butylene group;

$Am^+$ represents the radical

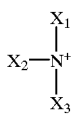

in which $X_1$, $X_2$ and $X_3$, together with the nitrogen atom to which they are attached, form an azabicyclic or azatricyclic ring system optionally substituted by a phenyl or benzyl group; and $A^-$ represents a pharmaceutically acceptable anion.

A particularly preferred compound of formula (VI) is (+) 1-[2-[3-(3,4-dichlorophenyl)-1-[(3-isopropoxyphenyl) acetyl]-3-piperidinyl]ethyl]4-phenyl-1-azabicyclo[2,2,2]octane; or a pharmaceutically acceptable salt, especially the chloride, thereof.

Another class of tachykinin antagonists of use in the present invention is that described in European Patent Specification No. 0 532 456, i.e. compounds of formula (VII):

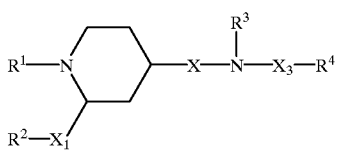

(VII)

or a pharmaceutically acceptable salt thereof, wherein $R^1$ represents an optionally substituted aralkyl, aryloxyalykl, heteroaralkyl, aroyl, heteroaroyl, cycloalkylcarbonyl, aralkanoyl, heteroarylalkanoyl, aralkoxycarbonyl or arylcarbamoyl group or the acyl group of an α-amino acid optionally N-substituted by a lower alkanoyl or carbamoyl-lower alkanoyl group;

$R^2$ represents cycloalkyl or an optionally substituted aryl or heteroaryl group;

$R^3$ represents hydrogen, alkyl, carbamoyl or an alkanoyl or alkenoyl group optionally substituted by carboxy or esterified or amidated carboxy;

$R^4$ represents an optionally substituted aryl group or an optionally partially saturated heteroaryl group;

$X_1$ represents methylene, ethylene, a bond, an optionally ketalised carbonyl group or an optionally etherified hydroxymethylene group;

$X_2$ represents alkylene, carbonyl or a bond; and $X_3$ represents carbonyl, oxo-lower alkyl, oxo(aza)-lower alkyl, or an alkyl group optionally substituted by phenyl, hydroxymethyl, optionally esterified or amidated carboxy, or (in other than the α-position) hydroxy.

A particularly preferred compound of formula (VII) is (2R', 4S')-2-benzyl-1-(3,5-dimethylbenzoyl)-N-(4-quinolinylmethyl)-4-piperidineamine; or a pharmaceutically acceptable salt thereof.

Another class of tachykinin antagonists of use in the present invention is that described in European Patent Specification No. 0 443 132, i.e. compounds of formula (VIII)

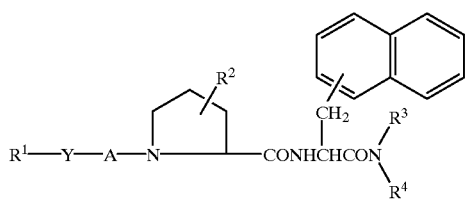

(VIII)

or a pharmaceutically acceptable salt thereof, wherein
$R^1$ is aryl, or a group of the formula:

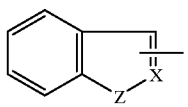

X is CH or N; and
Z is O or N—$R^5$, in which $R^5$ is hydrogen or lower alkyl;
$R^2$ is hydroxy or lower alkoxy;
$R^3$ is hydrogen or optionally substituted lower alkyl;
$R^4$ is optionally substituted ar(lower)alkyl;
A is carbonyl or sulfonyl; and
Y is a bond or lower alkenylene.

A particularly preferred compound of formula (VIII) is the compound of formula (VIIIa)

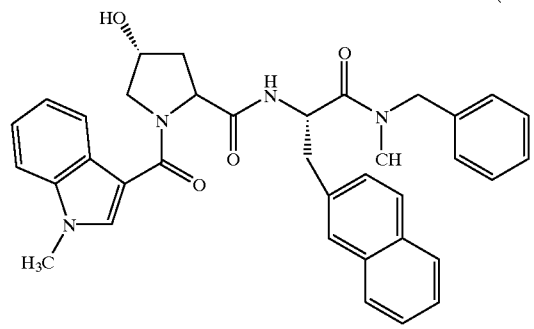

(VIIIa)

or a pharmaceutically acceptable salt thereof.

Another class of tachykinin antagonists of use in the present invention is that described in International Patent Specification No. WO 92/17449, i.e. compounds of the formula (IX)

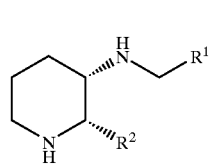

(IX)

or a pharmaceutically acceptable salt thereof, wherein
$R^1$ is aryl selected from indanyl, phenyl and naphthyl; heteroaryl selected from thienyl, furyl, pyridyl and quinolyl; and cycloalkyl having 3 to 7 carbon atoms, wherein one of said carbon atoms may optionally be replaced by nitrogen oxygen or sulfur; wherein each of said aryl and heteroaryl groups may optionally be substituted with one or more substituents, and said $C_{3-7}$cycloalkyl may optionally be substituted with one or two substituents, said substituents being independently selected from chloro, fluoro, bromo, iodo, nitro, $C_{1-10}$alkyl optionally substituted with from one to three fluoro groups, $C_{1-10}$alkoxy optionally substituted with from one to three fluoro groups, amino, $C_{1-10}$alkyl-S—, $C_{1-10}$alkyl-S(O)—, $C_{1-10}$alkyl-SO$_2$—, phenyl, phenoxy, $C_{1-10}$alkyl-SO$_2$NH—, $C_{1-10}$alkyl-SO$_2$NH—$C_{1-10}$akyl-, $C_{1-10}$alkylamino-di$C_{1-10}$alkyl-, cyano, hydroxy, cycloalkoxy having 3 to 7 carbon atoms, $C_{1-6}$alkylamino, $C_{1-6}$dialkylamino, HC(O)NH— and $C_{1-10}$alkyl-C(O)NH—; and $R^2$ is thienyl, benzhydryl, naphthyl or phenyl optionally substituted with from one to three substituents independently selected from chloro, bromo, fluoro, iodo, cycloalkoxy having 3 to 7 carbon atoms, $C_{1-10}$alkyl optionally substituted with from one to three fluoro groups and $C_{1-10}$alkoxy optionally substituted with from one to three fluoro groups.

A particularly preferred compound of formula (IX) is (2S,3S)-3-(2-methoxy-5-trifluoromethoxybenzyl)-amino-2-phenylpiperidine; or a pharmaceutically acceptable salt thereof.

Another class of tachykinin antagonists of use in the present invention is that described in International Patent Specification No. WO 95/06645, i.e. compounds of formula (X)

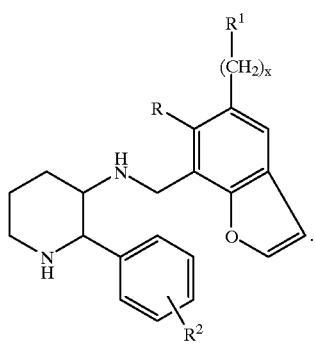

or a pharmaceutically acceptable salt thereof, wherein

R represents a hydrogen atom or a $C_{1-4}$alkoxy group;

$R^1$ is selected from phenyl, optionally substituted by a group —(CH$_2$)$_n$CONR$^3$R$^4$ or S(O)$_m$R$^3$; or a 5- or 6-membered aromatic heterocycle containing 1, 2, 3, or 4 heteroatoms selected from oxygen, nitrogen or sulphur, optionally substituted by a $C_{1-4}$alkyl, trifluoromethyl or cyano group or a group —(CH2)$_n$CONR$^3$R$^4$;

$R^2$ represents a hydrogen or halogen atom;

$R^3$ and $R^4$ independently represent hydrogen or $C_{1-4}$alkyl;

n represents zero, 1 or 2;

m represents zero, 1 or 2; and x represents zero or 1.

A particularly preferred compound of formula (X) is [5-(5-methyl-tetrazol-1-yl)-benzofuran-7-ylmethyl]-(2S-phenyl-piperidin-3S-yl)-amine; or a pharmaceutically acceptable salt thereof.

Another class of tachykinin antagonists of use in the present invention is that described in International Patent Specification No. WO 95/08549, i.e. compounds of formula (XI)

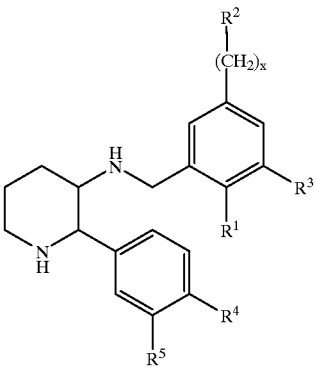

or a pharmaceutically acceptable salt thereof, wherein $R^1$ is a $C_{1-4}$alkoxy group;

$R^2$ is

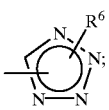

$R^3$ is a hydrogen or halogen atom;

$R^4$ and $R^5$ may each independently represent a hydrogen or halogen atom, or a $C_{1-4}$alkyl, $C_{1-4}$alkoxy or trifluoromethyl group;

$R^6$ is a hydrogen atom, a $C_{1-4}$alkyl, (CH$_2$)$_m$cyclopropyl, —S(O)$_n$C$_{1-4}$alkyl, phenyl, NR$^7$R$^8$, CH$_2$C(O)CF$_3$ or trifluoromethyl group;

$R^7$ and $R^8$ may each independently represent a hydrogen atom, or a $C_{1-4}$alkyl or acyl group;

x represents zero or 1;

n represents zero, 1 or 2; and m represents zero or 1.

Particularly preferred compounds of formula (XI) are (2-methoxy-5-tetrazol-1-yl-benzyl)-([2S,3S]-2-phenyl-piperidin-3-yl)-amine; and [2-methoxy-5-(5-trifluoromethyl-tetrazol-1-yl)-benzyl]-([2S,3S]-2-phenyl-piperidin-3-yl)-amine; or a pharmaceutically acceptable salt thereof.

Another class of tachykinin antagonists of use in the present invention is that described in International Patent Specification No. WO 95/14017, i.e. compounds of formula (XII)

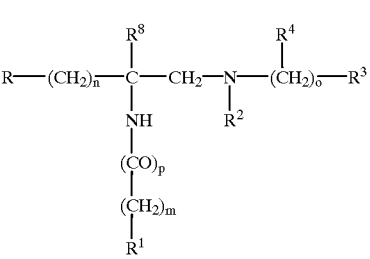

or a pharmaceutically acceptable salt thereof, wherein m is zero, 1, 2 or 3;

n is zero or 1;

o is zero, 1 or 2;

p is zero or 1;

R is phenyl, 2- or 3-indolyl, 2- or 3-indolinyl, benzothienyl, benzofuranyl, or naphthyl;

which R groups may be substituted with one or two halo, $C_{1-3}$alkoxy, trifluoromethyl, $C_{1-4}$alkyl, phenyl-$C_{1-3}$alkoxy, or $C_{1-4}$alkanoyl groups;

$R^1$ is trityl, phenyl, diphenylmethyl, phenoxy, phenylthio, piperazinyl, piperidinyl, pyrrolidinyl, morpholinyl, indolinyl, indolyl, benzothienyl, hexamethyleneiminyl, benzofuranyl, tetrahydropyridinyl, quinolinyl, isoquinolinyl, reduced quinolinyl, reduced isoquinolinyl, phenyl-($C_{1-4}$alkyl)-, phenyl-($C_{1-4}$alkoxy)-, quinolinyl-($C_{1-4}$alkyl)-, isoquinolinyl-($C_{1-4}$alkyl)-, reduced quinolinyl-($C_{1-4}$alkyl)-, reduced isoquinolinyl-($C_{1-4}$alkyl)-, benzoyl-($C_{1-3}$alkyl)-, $C_{1-4}$alkyl, or —NH—$CH_2$—$R^5$;

any one of which $R^1$ groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;

or any one of which $R^1$ groups may be substituted with phenyl, piperazinyl, $C_{3-8}$cycloalkyl, benzyl, $C_{1-4}$alkyl, piperidinyl, pyridinyl, pyrimidinyl, $C_{2-6}$alkanoylamino, pyrrolidinyl, $C_{2-6}$alkanoyl, or $C_{1-4}$alkoxycarbonyl;

any one of which groups may be substituted with halo, $C_{1-4}$alkyl, $C_{1-4}$alkoxy, trifluoromethyl, amino, $C_{1-4}$alkylamino, di($C_{1-4}$alkyl)amino, or $C_{2-4}$alkanoylamino;

or $R^1$ is amino, a leaving group, hydrogen, $C_{1-4}$alkylamino, or di($C_{1-4}$alkyl)amino;

$R^5$ is pyridyl, anilino-($C_{1-3}$alkyl)-, or anilinocarbonyl;

$R^2$ is hydrogen, $C_{1-4}$alkyl, $C_{1-4}$alkylsulfonyl, carboxy-($C_{1-3}$alkyl)-, $C_{1-3}$alkoxycarbonyl-($C_{1-3}$alkyl)-, or —CO—$R^6$;

$R^6$ is hydrogen, $C_{1-4}$alkyl, $C_{1-3}$haloalkyl, phenyl, $C_{1-3}$alkoxy, $C_{1-3}$hydroxyalkyl, amino, $C_{1-4}$alkylamino, di($C_{1-4}$alkyl)amino, or —$(CH_2)_q$—$R^7$;

q is zero to 3;

$R^7$ is carboxy, $C_{1-4}$alkoxycarbonyl, $C^{1-4}$alkylcarbonyloxy, amino, $C_{1-4}$alkylamino, di($C_{1-4}$alkyl)amino, $C_{1-6}$alkoxycarbonylamino, or phenoxy, phenylthio, piperazinyl, piperidinyl, pyrrolidinyl, morpholinyl, indolinyl, indolyl, benzothienyl, benzofuranyl, quinolinyl, phenyl-($C_{1-4}$alkyl)-, quinolinyl-($C_{1-4}$alkyl)-, isoquinolinyl-($C_{1-4}$alkyl)-, reduced quinolinyl-($C_{1-4}$alkyl)-, reduced isoquinolinyl-($C_{1-4}$-alkyl)-, benzoyl-$C_{1-3}$alkyl;

any one of which aryl or heterocyclic $R^7$ groups may be substituted with halo, trifluoromethyl, $C_{1-4}$alkoxy, $C_{1-4}$alkyl, amino, $C_{1-4}$alkylamino, di($C_{1-4}$alkyl)amino, or $C_{2-4}$alkanoylamino;

or any one of which $R^7$ groups may be substituted with phenyl, piperazinyl, $C_{3-8}$cycloalkyl, benzyl, piperidinyl, pyridinyl, pyrimidinyl, pyrrolidinyl, $C_{2-6}$alkanoyl, or $C_{1-4}$alkoxycarbonyl;

any of which groups may be substituted with halo, trifluoromethyl, amino, $C_{1-4}$alkoxy, $C_{1-4}$alkyl, $C_{1-4}$alkylamino, di($C_{1-4}$alkyl)amino, or $C_{2-4}$alkanoylamino;

$R^8$ is hydrogen or $C_{1-6}$alkyl;

$R^3$ is phenyl, phenyl-($C_{1-6}$alkyl)-, $C_{3-8}$cycloalkyl, $C_{5-8}$cycloalkenyl, $C_{1-8}$alkyl, naphthyl, $C_{2-8}$alkenyl, or hydrogen;

any one or which groups except hydrogen may be substituted with one or two halo, $C_{1-3}$alkoxy, $C_{1-3}$alkylthio, nitro, trifluoromethyl, or $C_{1-3}$alkyl groups; and $R^4$ is hydrogen or $C_{1-3}$alkyl;

with the proviso that if $R^1$ is hydrogen or halo, $R^3$ is phenyl, phenyl-($C_{1-6}$alkyl)-, $C_{3-8}$cycloalkyl, $C_{5-8}$cycloalkenyl, or naphthyl.

A particularly preferred compound of formula (XII) is [N-(2-methoxybenzyl)acetylamino]-3-(1H-indol-3-yl)-2-[N-(2-(4-piperidin-1-yl)piperidin-1-yl)acetylamino] propane; or a pharmaceutically acceptable salt thereof.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl, n-butyl, sec-butyl and tert-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

A particular aryl-$C_{1-6}$alkyl, e.g. phenyl-$C_{1-6}$alkyl, group is benzyl.

Suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups.

The term "halogen" as used herein includes fluorine, chlorine, bromine and iodine.

The compounds of use in this invention may have one or more asymmetric centres and can therefore exist as enantiomers and possibly as diastereoisomers. It is to be understood that the present invention relates to the use of all such isomers and mixtures thereof.

Suitable pharmaceutically acceptable salts of the tachykinin antagonists of use in the, present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid or phosphoric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

Suitable opioid analgesics of use in the present invention include morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

A particularly preferred opioid analgesic of use in the present invention is morphine; or a pharmaceutically acceptable salt thereof.

Suitable pharmaceutically acceptable salts of the opioid analgesics of use in the present invention include those salts described above in relation to the salts of tachykinin antagonists.

Preferred salts of opioid analgesics of use in the present invention include morphine sulphate, morphine hydrochloride, morphine tartrate, codeine phosphate, codeine sulphate, dihydrocodeine bitartrate, diacetylmorphine hydrochloride, hydrocodone bitartrate, hydromorphone hydrochloride, levorphanol tartrate, oxymorphone hydrochloride, alfentanil hydrochloride, buprenorphine hydrochloride, butorphanol tartrate, fentanyl citrate, meperidine hydrochloride, methadone hydrochloride, nalbuphine hydrochloride, propoxyphene hydrochloride, propoxyphene napsylate (2-naphthalenesulphonic acid (1:1) monohydrate), and pentazocine hydrochloride.

A particularly preferred opioid analgesic of use in the present invention is morphine sulphate.

As stated above, the tachykinin antagonist and opioid analgesic may, be formulated in a single pharmaceutical composition or alternatively in individual pharmaceutical compositions for simultaneous, separate or sequential use in accordance with the present invention.

Preferably the compositions according to the present invention are in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

Preferred compositions for administration by injection include those comprising a tachykinin antagonist, as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween™ 20, 40, 60, 80 or. 85) and other sorbitans (e.g. Span™ 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion will preferably comprise fat droplets between 0.1 and 1.0 $\mu$m, particularly 0.1 and 0.5$\mu$m, and have a pH in the range of 5.5 to 8.0.

Particularly preferred emulsion compositions are those prepared by mixing a tachykinin antagonist with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

The present invention futher provides a process for the preparation of a pharmaceutical composition comprising a tachykinin antagonist and an opioid analgesic, which process comprises bringing a tachykinin antagonist and an opioid analgesic into association with a pharmaceutically acceptable carrier or excipient.

When administered in combination, either as a single or as separate pharmaceutical composition(s), the tachykinin antagonist and the opioid analgesic are presented in a ratio which is consistent with the manifestation of the desired effect. In particular, the ratio by weight of the tachykinin antagonist to the opioid analgesic will suitably be approximately 1 to 1. Preferably this ratio will be between 0.001 to 1 and 1000 to 1, and especially between 0.01 to 1 and 100 to 1.

A suitable dosage level for the tachykinin antagonist is about 0.001 to 25 mg/kg per day, preferably about 0.005 to 10 mg/kg per day, and especially about 0.005 to 5 mg/kg per day. The compounds may be administered on a regimen of up to 6 times per day, preferably 1 to 4 times per day.

The opioid analgesic may be administered at a dosage level up to conventional dosage levels for such analgesics, but preferably at a reduced level in accordance with the present invention. Suitable dosage levels will depend upon the analgesic effect of the chosen opioid analgesic, but typically suitable levels will be about 0.001 to 25 mg/kg per day, preferably 0.005 to 10 mg/kg per day, and especially 0.005 to 5 mg/kg per day. The compound may be administered on a regimen of up to 6 times per day, preferably 1 to 4 times per day.

It will be appreciated that the amount of a tachykinin antagonist and opioid analgesic required for use in the treatment or prevention of pain or nociception will vary not only with the particular compounds or compositions selected but also with the route of administration, the nature of the condition being treated, and the age and condition of the patient, and will ultimately be at the discretion of the attendant physician.

The compounds of formulae (I), (IV), (V), (VI), (VII) and (VIII) may be prepared by the methods described in EP-A-0 577 394, EP-A-0 436 334, WO-A-93/21155, EP-A-0 591 040, EP-A-0 532 456 and EP-A-0 443 132, respectively.

The compounds of formula (II) may be prepared by a variety of methods, thus, according to a general process, the compounds of formula (II) may be prepared from compounds of formula (A)

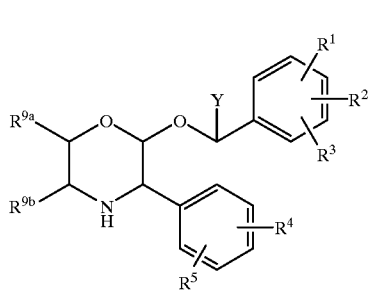

(A)

wherein $R^1$, $R^2$, $R^3$, $R^4$, $R^5$, $R^{9a}$, $R^{9b}$ and Y are as defined in relation to formula (II) by reaction with a compound of formula (B):

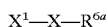 (B)

where X is as defined in relation to formula (II), $R^{6a}$ is a group of the formula $R^6$ as defined in relation to formula (II) or a precursor therefor and $X^1$ is a leaving group such as bromine or chlorine; and, if $R^{6a}$ is a precursor group, converting it to a group $R^6$ (in which process any reactive group may be protected and thereafter deprotected if desired).

This reaction may be performed in conventional manner, for example in an organic solvent such as dimethylformamide in the presence of an acid acceptor such as potassium carbonate.

According to another process, compounds of formula (II) wherein $R^6$ represents 1,2,3-triazol-4-yl substituted by $CH_2NR^7R^8$, and X is —$CH_2$—, may be prepared by reaction of a compound of formula (C):

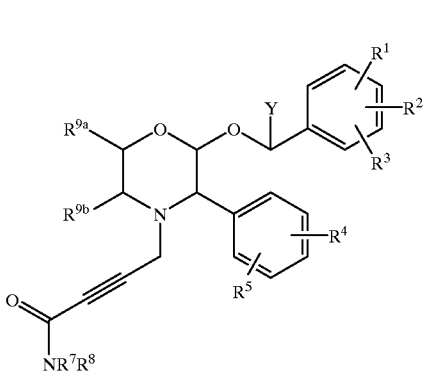

(C)

with an azide, for example, sodium azide in a suitable solvent such as dimethylsulphoxide at a temperature of between 40° C. and 100° C., followed by reduction of the carbonyl group adjacent to —$NR^7R^8$ using a suitable reducing agent such as lithium aluminium hydride at at a temperature between −10° C. and room temperature, conveniently at room temperature.

Alternatively, according to another process, compounds of formula (II) wherein $R^6$ represents 1,2,3-triazol-4-yl substituted by $CH_2NR^7R^8$, and X is —$CH_2$—, may be prepared by reaction of a compound of formula (D)

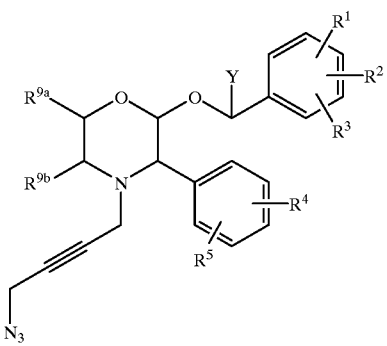

(D)

with an amine of formula $NHR^7R^8$, in a suitable solvent such as an ether, for example, dioxan, at elevated temperature, for example, between 50° C. and 100° C., in a sealed tube, or the like. This reaction is based upon that described in *Chemische Berichte* (1989) 122, p. 1963.

According to another process, compounds of formula (II) wherein $R^6$ represents substituted or unsubstituted 1,3,5-triazine may be prepared by reaction of intermediates of formula (E):

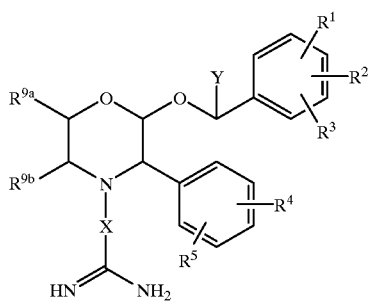

(E)

with substituted or unsubstituted 1,3,5-triazine.

The reaction is conveniently effected in a suitable organic solvent, such as acetonitrile, at elevated temperature, such as 80–90° C., preferably about 82° C.

According to a further process, compounds of formula (II) wherein R⁶ represents substituted or unsubstituted 1,2,4-triazine may be prepared by reaction of an intermediate of formula (F) with a dicarbonyl compound of formula (G):

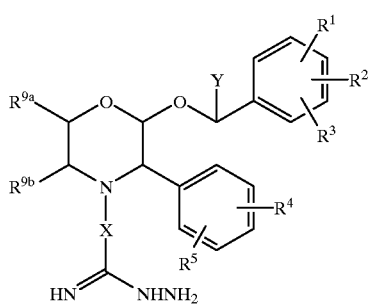

(F)

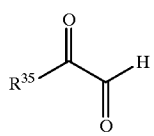

(G)

wherein R³⁵ represents H or a suitable substituent such as ZNR⁷R⁸.

The reaction is conveniently effected in a suitable organic solvent, such as an ether, e.g. tetrahydrofuran, conveniently at ambient temperature.

According to a further process, compounds of formula (II) wherein R⁶ represents a substituted 1,2,4-triazolyl group may be prepared by reaction of an intermediate of formula (A) with a compound of formula (H)

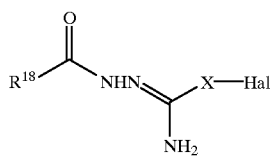

(H)

wherein X is as defined in relation to formula (II), Hal is a halogen atom, for example, bromine, chlorine or iodine and R¹⁸ is H, CONH₂ or OCH₃ (which is converted to an oxo substituent under the reaction conditions) in the presence of a base, followed where necessary by conversion to a compound of formula (II), for example, by reduction of the CONH₂ group to CH₂NH₂.

Suitable bases of use in the reaction include alkali metal carbonates such as, for example, potassium carbonate. The reaction is conveniently effected in an anhydrous organic solvent such as, for example, anhydrous dimethylformamide, preferably at elevated temperature, such as about 140° C.

A suitable reducing agent for the group CONH₂ is lithium aluminium hydride, used at between –10° C and room temperature.

According to another process, compounds of formula (II) wherein R⁶ represents thioxotriazolyl may be prepared from intermediates of formula (J):

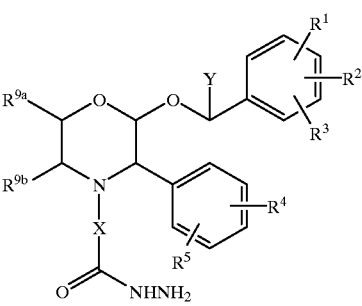

(J)

by reaction with a compound of formula HNCS, in the presence of a base.

Suitable bases of use in the reaction include organic bases such as, for example, 1,8-diazabicyclo[5.4.0]undec-7-ene (DBU). The reaction is conveniently effected in a suitable orgainc solvent, such as alcohol, e.g. butanol.

Compounds of formula (II) may also be prepared from other compounds of formula (II) using suitable interconversion procedures. For example, compounds of formula (II) wherein X represents C₁₋₄alkyl may be prepared from compounds of formula (II) wherein X represents C₁₋₄alkyl substituted by oxo by reduction, for example, using borane or lithium aluminium hydride. Suitable interconversion procedures will be readily apparent to those skilled in the art.

Intermediates of formula (C) may be prepared from intermediates of formula (A) by reaction with an acetylene compound of formula HC≡C—CH₂-Hal in the presence of a base such as potassium carbonate in a suitable solvent such as dimethylformamide, conveniently at room temperature, followed by reaction of the resultant acetylene intermediate with an amide of formula Hal-CO—NR⁷R⁸ in the presence of suitable catalysts including bis(triphenylphosphine) palladium(II) chloride, copper(I) iodide and triphenylphosphine in a suitable solvent such as triethylamine, preferably at reflux.

Intermediates of formula (D) may be prepared from a compound of formula (K):

(K)

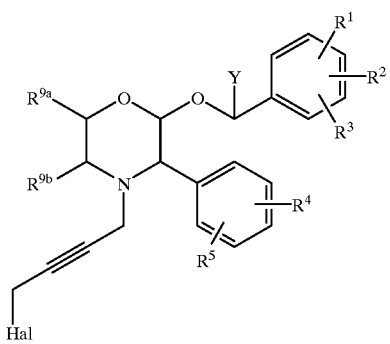

wherein Hal is a halogen atom, for example, chlorine, bromine or iodine, especially chlorine, by reaction with an azide, for example, sodium azide in a suitable solvent such as dimethylsulphoxide at a temperature between 40° C. and 100° C.

Compounds of formula (K) may be prepared by a dropwise addition of an intermediate of formula (A) to a dihaloacetylene of formula Hal—$CH_2$—C≡C—$CH_2$-Hal where each Hal is independently chlorine, bromine or iodine, especially chlorine. The reaction is conveniently effected in a suitable solvent such as dimethylformamide in the presence of a base such as potassium carbonate.

Intermediates of formula (E) may be prepared from intermediates of formula (A) by reaction with a compound of formula Hal-X—C(NH)$NH_2$, where Hal and X are as previously defined.

Intermediates of formula (F) may be prepared from intermediates of formula (A) by reaction with a compound of formula Hal-X—C(NH)NHNH-Boc, wherein Hal and X are as previously defined and Boc stands for t-butoxycarbonyl, followed by deprotection under acidic conditions.

Compounds of formula (G) are commercially available or may be prepared from commercially available compounds by known methods.

Compounds of formula (H) may be prepared as described in *J. Med. Chem.*, 27, 849 (1984).

Intermediates of formula (J) may be prepared from the corresponding ester by treatment with hydrazine. The reaction is conveniently effected in a suitable organic solvent, such as an alcohol, for example, ethanol, at elevated temperature.

For compounds wherein $R^6$ is a heterocycle substituted by a $ZNR^7R^8$ group where Z is $CH_2$, certain favoured compounds of formula (II) may be prepared from a corresponding compound with a hydrogen atom in place of the $ZNR^7R^8$. Thus, for example a compound of the formula (II) wherein $R^6$ is an imidazolinone group carrying a $CH_2NR^7R^8$ moiety may be prepared from a corresponding compound lacking the $CH_2NR^7R^8$ moiety by reaction with formaldehyde and an amine $NHR^7R^8$ under conventional Mannich reaction conditions, for example in methanol with heating. If desired, a pre-formed reagent such as $R^7R^8N^+$=$CH_2$.I— may be employed and a tertiary amine such as triethylamine used as acid acceptor.

Alternatively a compound of formula (II) wherein $R^6$ is an imidazolinone group lacking a $CH_2NR^7R^8$ may be reacted with paraformaldehyde and an amine for example a secondary amine such as pyrrolidine or morpholine to give a compound wherein the imidazolinone ring is substituted by $CH_2NR^7R^8$ where $R^7$, $R^8$ and the nitrogen atom to which they are attached form a heteroaliphatic ring of 4 to 7 ring atoms which may optionally contain an oxygen ring atom or a second nitrogen atom which will be part of a NH or $NR^c$ moiety, where $R^c$ is as defined in formula (II).

This reaction may be performed in a conventional manner, for instance, in a suitable solvent such as an alcohol, for example, methanol at an elevated temperature up to the boiling point of the solvent.

A further alternative method for the preparation of certain compounds of formula (II) involves the reaction of an intermediate of formula (A) as defined above with one of the compounds of formula (L):

(L)

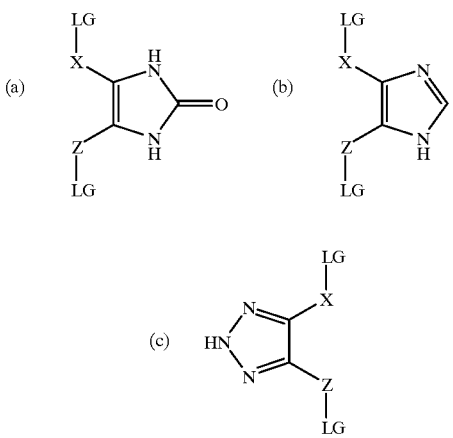

wherein each LG, which may be the same or different, is a leaving group, such as an alkyl- or arylsulphonyloxy group (e.g. mesylate or tosylate) or a halogen atom, (e.g. bromine, chlorine or iodine), and X and Z are as defined in formula (II), followed by reaction of the resultant compound with an amine $NHR^7R^8$ to complete the $ZNR^7R^8$ moiety if desired.

This reaction is conveniently effected in an organic solvent such as dimethylformamide in the presence of an acid acceptor such as potassium carbonate.

It will be appreciated that, where necessary, reactive groups may be protected, thus for example, the NH groups of an imidazolinone of formula (La) may be protected by any suitable amine protecting group such as an acetyl group.

The preferred phosphate prodrugs of the compounds of formula (II) may be prepared in a stepwise manner from a compound of formula (II) wherein Y is, for example, —$CH_2$OH—.

Thus, the hydroxy compound is first treated with dibenzyloxydiethylamino-phosphine in a suitable solvent such as tetrahydrofuran, preferably in the presence of an acid catalyst such as tetrazole. The resultant compound (where Y=$CH_2$OP(O$CH_2$Ph)$_2$) is then oxidised using, for example, 4-methylmorpholine-N-oxide to give the dibenzyl-protected phosphate. Deprotection by catalytic hydrogenation or transfer hydrogenation (palladium catalyst on carbon and ammonium formate), in a suitable solvent such as methanol at reflux, yields the desired phosphate prodrug which may be converted to any desired salt form by conventional methodology.

In an alternative two-step method, the hydroxy compound of formula (II) may be reacted with a suitable reducing agent such as sodium hydride in tetrahydrofuran, and tetrabenzylpyrophosphate added to yield the dibenzyl-protected phosphate which may be deprotected as described above.

The compounds of the formula (A) may be prepared as shown in Scheme 1 in which $Ar^1$ represents the $R^1$, $R^2$, $R^3$ substituted phenyl group; $Ar^2$ represents the $R^4$, $R^5$ substituted phenyl group and Ph represents phenyl:

Scheme 1

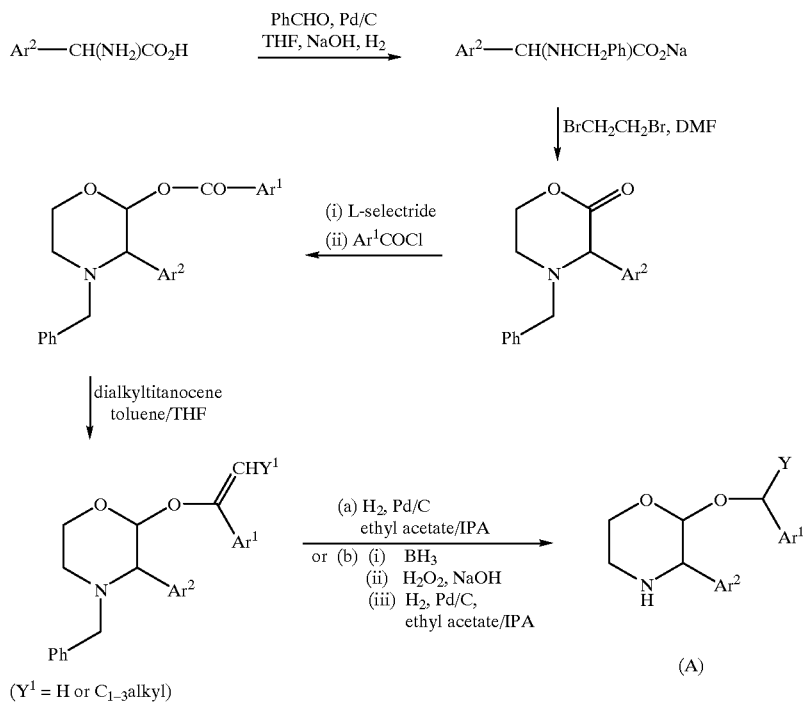

($Y^1$ = H or $C_{1-3}$alkyl)

The following references describe methods which may be applied by the skilled worker to the chemical synthesis set forth above once the skilled worker has read the disclosure herein.

(i) D. A. Evans et al., *J. Am. Chem. Soc.*, (1990) 112, 4011.
(ii) I. Yanagisawa et al., *J. Med. Chem.*, (1984) 27, 849.
(iii) R. Duschinsky et al., *J. Am. Chem. Soc.*, (1948) 70, 657.
(iv) F. N. Tebbe et al., *J. Am. Chem. Soc.*, (1978) 100, 3611.
(v) N. A. Petasis et al., *J. Am. Chem. Soc.*, (1990) 112, 6532.
(vi) K. Takai et al, *J. Org. Chem.*, (1987) 52, 4412.

The Examples disclosed herein produce predominantly the preferred isomers. The unfavoured isomers are also produced as minor components. If desired they may be isolated and employed to prepare the various stereoisomers in conventional manner, for example chromatography using an appropriate chiral column. However, the skilled worker will appreciate that although the Examples have been optimized to the production of the preferred isomers, variation in solvent, reagents, chromatography etc can be readily employed to yield the other isomers.

L-Selectride is lithium tri-sec-butylborohydride.

It will be appreciated that compounds of the formula (II) wherein $R^6$ contains an =O or =S substituent can exist in tautomeric forms. All such tautomeric forms and mixtures thereof are included within this invention. Most aptly the =O or =S substituent in $R^6$ is the =O substituent.

Where they are not commercially available, the intermediates of formula (B) above may be prepared by procedures which will be readily apparent to one skilled in the art.

The compounds of formula (III) may be prepared by conventional methods using methodology described above for compounds of formula (II), and those described in EP-A-0 577 394. The following schemes and description (in which the various substituents are as defined in formula (III)) also serve to illustrate suitable methods:

Scheme 2

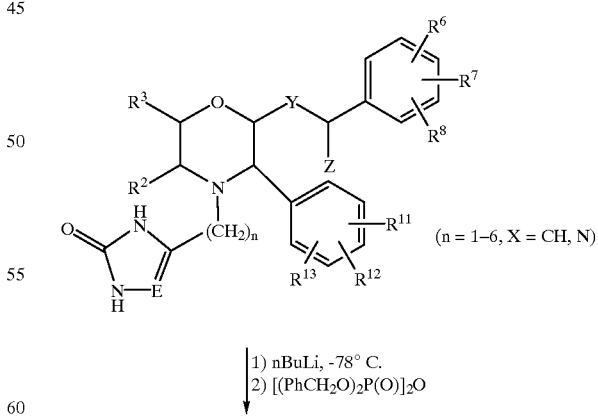

(n = 1–6, X = CH, N)

1) nBuLi, -78° C.
2) [(PhCH$_2$O)$_2$P(O)]$_2$O

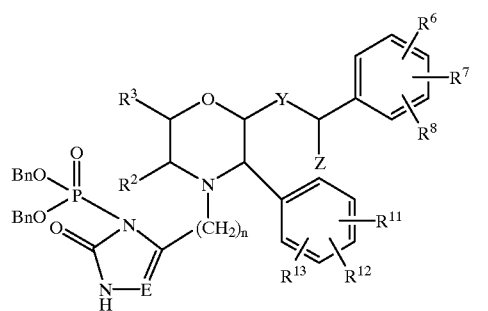
H₂, 5% Pd/C
MeOH, H₂O,
KHCO₃
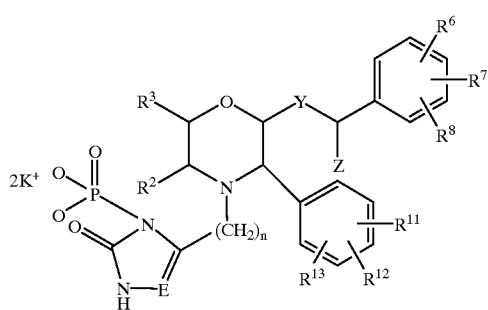
Scheme 3
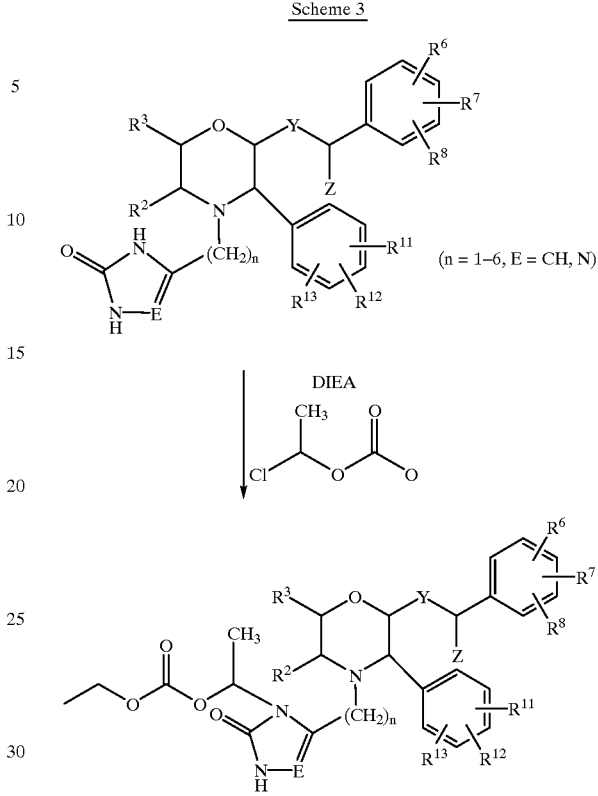
(n = 1–6, E = CH, N)
DIEA
SCHEME 4
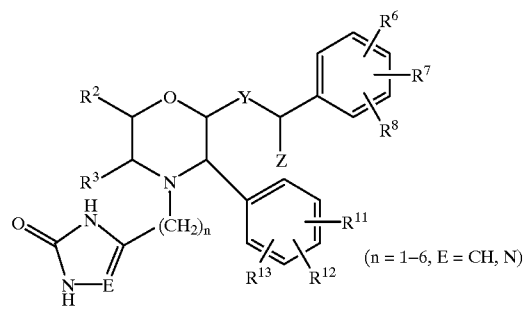
(n = 1–6, E = CH, N)
(iPr)₂NEt -continued
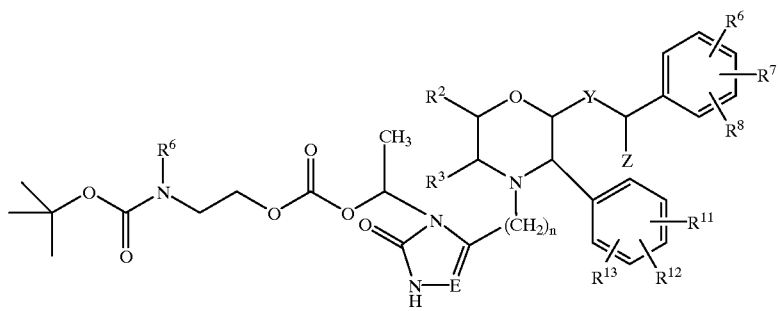
↓ CF₃CO₂H, CH₂Cl₂
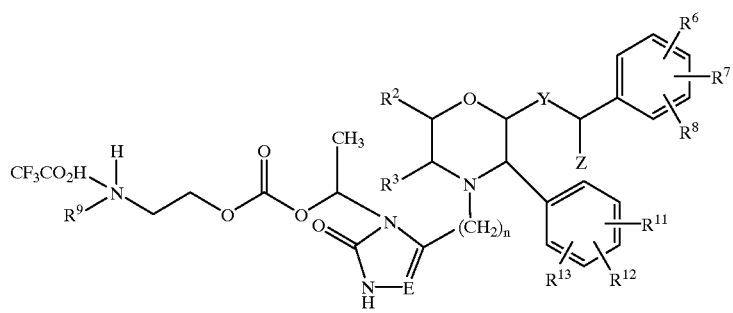
Scheme 5
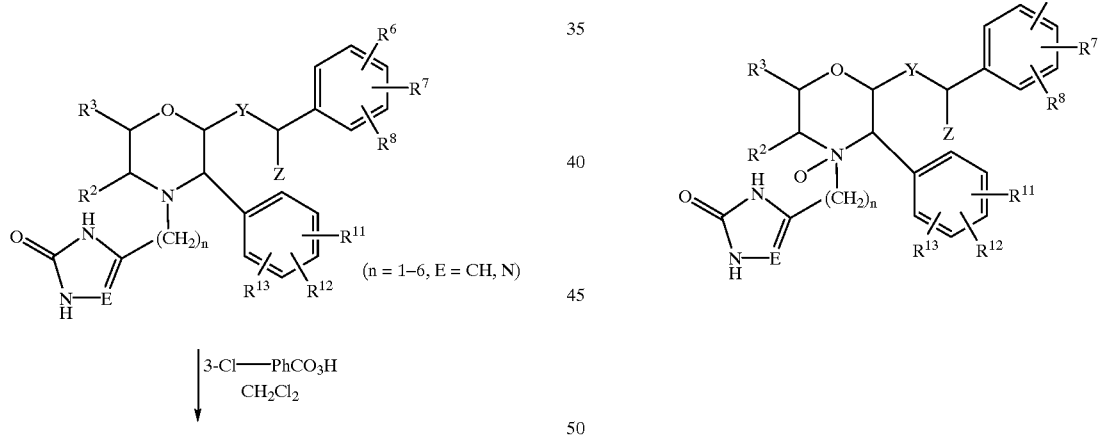
(n = 1–6, E = CH, N)
↓ 3-Cl—PhCO₃H
CH₂Cl₂
-continued

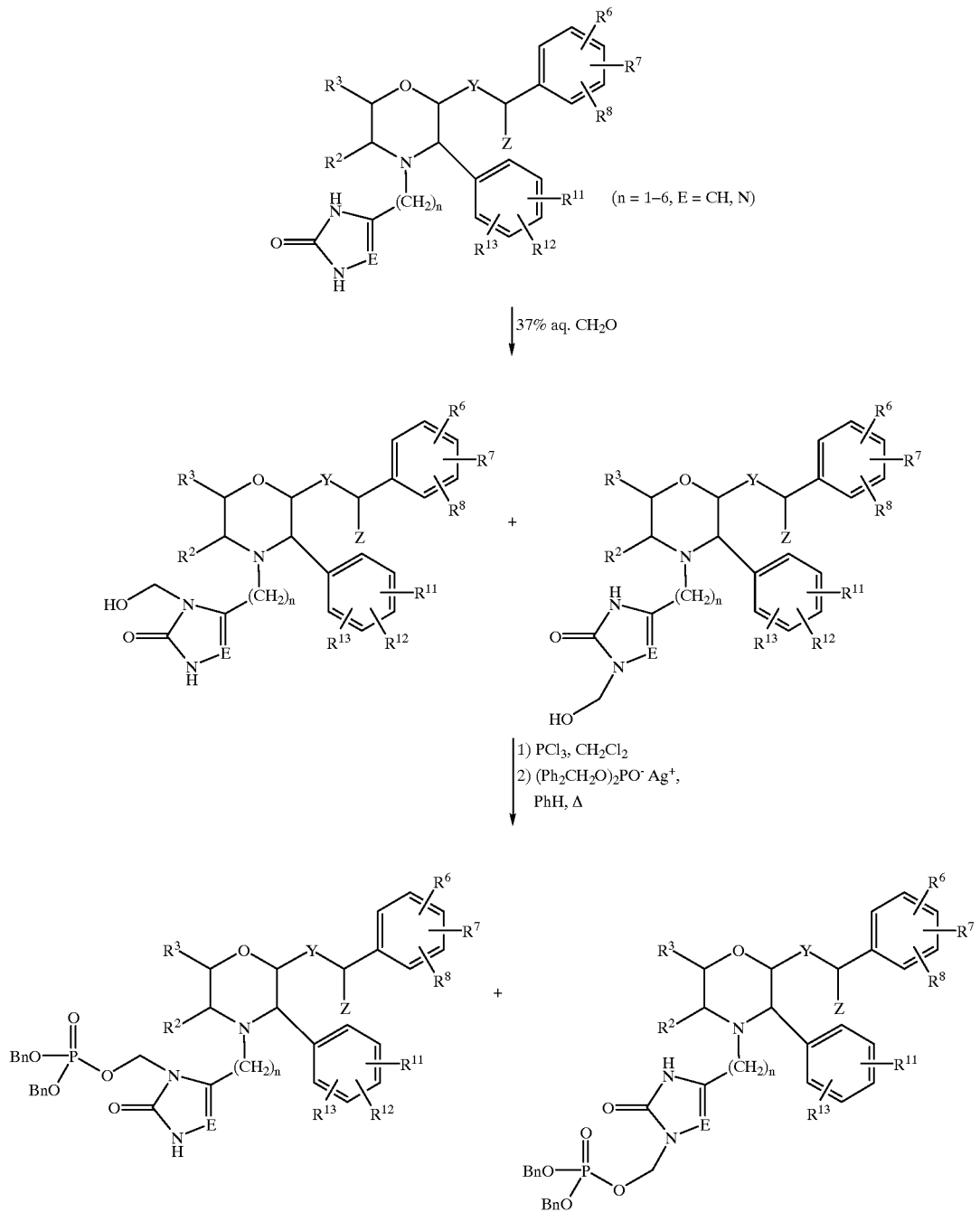

Scheme 7

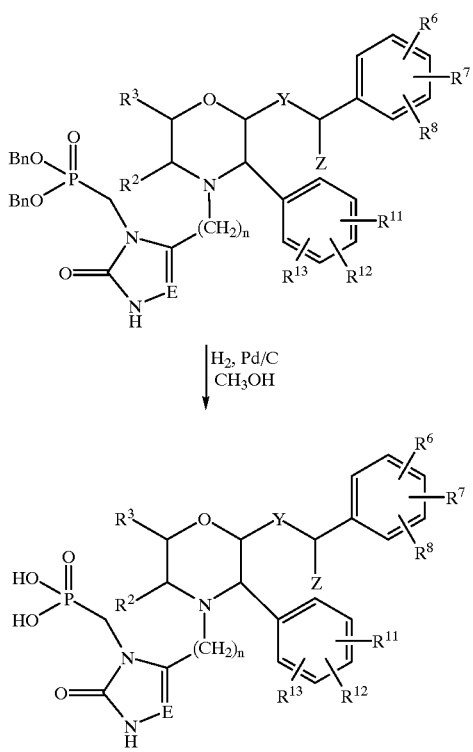

Scheme 8

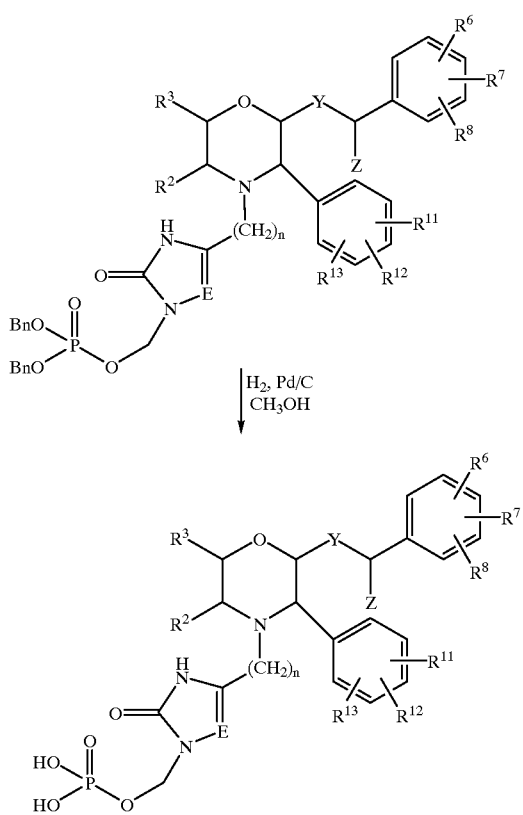

As depicted in Scheme 2, treatment of, for example, a triazolone or imidazolone-containing tachykinin antagonist with a suitable base, such as n-butyllithium, sodium hydride, potassium hydride, lithium hexamethyldisilazide, sodium hexamethyldisilazide, potassium hexamethyldisilazide or lithium diisoporpylamine in THF at low temperature followed by addition of an appropriate phosphoryl transfer reagent, for example, tetrabenzyl pyrophosphate, dibenzyl phosphochloridate or dibenzyl phosphofluoridate provides an intermediate with a protected phosphoryl group. Following purification, for example by gravity silica gel chromatography, the dibenzyl ester may be converted into the desired product by hydrogenolysis, for example with hydrogen gas in the presence of palladium on carbon in the presence of two equivalents of a suitable salt forming agent, such as sodium bicarbonate (to prepare the disodium salt of the phosphoramidate product) or potassium bicarbonate (to prepare the dipotassium salt of the product). The product may be purified by crystallization or by normal or reverse phase chromatography.

As depicted in Scheme 3, treatment of, for example, a triazolone or imidazolone-containing tachykinin antagonist with a suitable base, such as diisopropylethylamine, 2,6-dimethylpyridine or triethylamine and 1-chloroethyl ethyl carbonate in a compatible solvent such as toluene or dichloroethane, followed by heating the mixture at reflux for 12–24 hr, provides the corresponding N-alkylcarbonate product, which may be purified by flash chromatography.

Similarly, the same substrate may be treated with the functionalized carbonate given in Scheme 4 under similar conditions, such as refluxing in toluene in the presence of diisopropylethylamine, 2,6-dimethylpyridine or triethylamine to provide the N-Boc protected intermediate. Cleavage of the Boc group, for example with trifluoroacetic acid in methylene chloride or with hydrogen chloride in ethyl acetate provides the corresponding salt of the prodrug product.

Generation of the N-oxide prodrug of the aforementioned morpholine tachykinin antagonists may be achieved as shown in Scheme 5 simply by treatment with an oxygen-transfer agent, such as a peracid, such as 3-chloroperoxybenzoic acid of trifluoromethylperacetic acid, or with hydrogen peroxide or alkyl hydroperoxides such as t-butyl hydroperoxide in the presnce of a transition metal catalyst, or with Caro's acid ($H_2SO_5$).

Compounds containing linking groups between the heterocycle and the phosphoryl group may also be prepared, for example as illustrated in Scheme 6 (see S. A. Varia et al, *J. Pharm. Sci.*, (1984) 73, 1068–1073). Treatment of the parent compound with an aliphatic aldehyde, for example aqueous formaldehyde, provides the corresponding hydroxymethyl derivatives, which after conversion to the chloride with phosphorus trichloride, may be treated with silver dibenzyl phosphate. The resulting protected phosphates may be separated by conventional means, for example silica gel chromatography. The purified products may then be converted to the free phosphoric acids as depicted in Schemes 7 and 8, by treatment with a reducing agent such as hydrogen gas in the presence of pallidium on carbon.

The compounds of formula (III) obtained according to the reactions as explained above may be isolated and purified in a conventional manner, for example, extraction, precipitation, fractional crystallization, recrystallization, chromatography, and the like.

During any of the above synthetic sequences it may be necessary and/or desirable to protect sensitive or reactive groups on any of the molecules concerned. This may be achieved by means of conventional protecting groups, such as those described in *Protective Groups in Organic Chemistry,* ed. J. F. W. McOmie, Plenum Press, 1973; and T. W. Greene and P. G. M. Wuts, *Protective Groups in Organic Synthesis,* John Wiley & Sons, 1991. The protecting groups may be removed at a convenient subsequent stage using methods known from the art.

In addition to the above synthetic methods and the teaching in the prior art referenced above, the following non-limiting examples describe the preparation of specific tachykinin antagonists of use in the present invention:

Description 1

(S)-(4-Fluorophenyl)glycine
Via Chiral Synthesis

Step A: 3-(4-Fluorophenyl)acetyl-4-(S)-benzyl-2-oxazolidinone

An oven-dried, 1 L 3-necked flask, equipped with a septum, nitrogen inlet, thermometer, and a magnetic stirring bar, was flushed with nitrogen and charged with a solution of 5.09 g (33.0 mmol) of 4-fluorophenylacetic acid in 100 ml of anhydrous ether. The solution was cooled to −10° C. and treated with 5.60 ml (40.0 mmol) of triethylamine followed by 4.30 ml (35.0 mmol) of trimethylacetyl chloride. A white precipitate formed immediately. The resulting mixture was stirred at −10° C. for 40 minutes, then cooled to −78° C.

An oven-dried, 250 ml round bottom flask, equipped with a septum and a magnetic stirring bar, was flushed with nitrogen and charged with a solution of 5.31 g (30.0 mmol) of 4-(S)-benzyl-2-oxazolidinone in 40 ml of dry THF. The solution was stirred in a dry ice/acetone bath for 10 minutes, then 18.8 ml of 1.6M n-butyllithium solution in hexanes was slowly added. After 10 minutes, the lithiated oxazolidinone solution was added, via cannula, to the above mixture in the 3-necked flask. The cooling bath was removed from the resulting mixture and the temperature was allowed to rise to 0° C. The reaction was quenched with 100 ml of saturated aqueous ammonium chloride solution, transferred to a 1 l flask, and the ether and THF were removed in vacuo. The concentrated mixture was partitioned between 300 ml of methylene chloride and 50 ml of water and the layers were separated. The organic layer was washed with 100 ml of 2N aqueous hydrochloric acid solution, 300 ml of saturated aqueous sodium bicarbonate solution, dried over magnesium sulfate and concentrated in vacuo. Flash chromatography on 400 g of silica gel using 3:2 v/v hexanes/ether as the eluant afforded 8.95 g of an oil that slowly solidified on standing. Recrystallisation from 10:1 hexanes/ether afforded 7.89 g (83%) of the title compound as a white solid: $^1$H NMR (400 MHz, CDCl$_3$) δ2.76 (1H, dd, J=13.2, 9.2 Hz), 3.26 (dd, J=13.2, 3.2 Hz), 4.16–4.34 (4H, m), 4.65 (1H, m), 7.02–7.33 (9H, m).

Analysis Calcd. for C$_{18}$H$_{16}$FNO$_3$: C, 69.00; H, 5.15; N, 4.47; F, 6.06; Found: C, 68.86; H, 5.14; N, 4.48; F, 6.08%.

Step B: 3-((S)-Azido-(4-fluorophenyl))acetyl-4-(S)-benzyl-2-oxazolidinone

An oven-dried, 1 litre 3-necked flask, equipped with a septum, nitrogen inlet, thermometer, and a magnetic stirring bar, was flushed with nitrogen and charged with a solution of 58.0 ml of 1M potassium bis(trimethylsilyl)amide solution in toluene and 85 ml of THF and was cooled to −78° C. An oven-dried 250 ml round-bottomed flask, equipped with a septum and a magnetic stirring bar, was flushed with nitrogen and charged with a solution of 7.20 g (23.0 mmol) of 3-(4-fluorophenyl)acetyl-4-(S)-benzyl-2-oxazolidinone (from Step A) in 40 ml of THF. The acyl oxazolidinone solution was stirred in a dry ice/acetone bath for 10 minutes, then transferred, via cannula, to the potassium bis (trimethylsilyl)amide solution at such a rate that the internal temperature of the mixture was maintained below −70° C. The acyl oxazolidinone flask was rinsed with 15 ml of THF and the rinse was added, via cannula, to the reaction mixture and the resulting mixture was stirred at −78° C. for 30 minutes. An oven-dried, 250 ml round-bottomed flask, equipped with a septum and a magnetic stirring bar, was flushed with nitrogen and charged with a solution of 10.89 g (35.0 mmol) of 2,4,6-triisopropylphenylsulfonyl azide in 40 ml of THF. The azide solution was stirred in a dry ice/acetone bath for 10 minutes, then transferred, via cannula, to the reaction mixture at such a rate that the internal temperature of the mixture was maintained below −70° C. After 2 minutes, the reaction was quenched with 6.0 ml of glacial acetic acid, the cooling bath was removed and the mixture was stirred at room temperature for 18 hours. The quenched reaction mixture was partitioned between 300 ml of ethyl acetate and 300 ml of 50% saturated aqueous sodium bicarbonate solution. The organic layer was separated, dried over magnesium sulfate, and concentrated in vacuo. Flash chromatography on 500 g of silica gel using 2:1 v/v, then 1:1 v/v hexanes/methylene chloride as the eluant afforded 5.45 g (67%) of the title compound as an oil. $^1$H NMR (400 MHz, CDCl$_3$) δ2.86 (1H, dd, J=13.2, 9.6 Hz), 3.40 (1H, dd, J=13.2, 3.2 Hz), 4.09–4.19 (2H, m), 4.62–4.68 (1H, m), 6.14 (1H, s), 7.07–7.47 (9H, m)

Analysis Calcd. for C$_{18}$H$_{15}$FN$_4$O$_3$: C, 61.01; H, 4.27; N, 15.81; F, 5.36; Found: C, 60.99; H, 4.19; N, 15.80; F, 5.34%.

Step C: (S)-Azido-(4-fluorophenyl)acetic acid

A solution of 5.40 g (15.2 mmol) of 3-((S)-azido-(4-fluorophenyl))acetyl-4-(S)-benzyl-2-oxazolidinone (from step B) in 200 ml of 3:1 v/v THF/water was stirred in an ice bath for 10 minutes. 1.28 g (30.4 mmol) of lithium hydroxide monohydrate was added in one portion and the resulting mixture was stirred cold for 30 minutes. The reaction mixture was partitioned between 100 ml of methylene chloride and 100 ml of 25% saturated aqueous sodium bicarbonate solution and the layers were separated. The aqueous layer was washed with 2×100 ml of methylene chloride and acidified to pH 2 with 2N aqueous hydrochloric acid solution. The resulting mixture was extracted with 2×100 ml of ethyl acetate; the extracts were combined, washed with 50 ml of saturated aqueous sodium chloride solution, dried over magnesium sulfate, and concentrated in vacuo to afford 2.30 g (77%) of the title compound as an oil that was used in the following step without further purification. IR Spectrum (neat, cm$^{-1}$): 2111, 1724. $^1$H NMR (400 MHz, CDCl$_3$) δ5.06 (1H, s), 7.08–7.45 (4H, m), 8.75 (1H, br s).

Step D: (S)-(4-Fluorophenyl)glycine

A mixture of 2.30 g (11.8 mmol) of (S)-azido-(4-fluorophenyl)acetic acid (from Step C), 250 mg 10% palladium on carbon catalyst and 160 ml 3:1 v/v water/acetic acid was stirred under an atmosphere of hydrogen for 18 hours. The reaction mixture was filtered through Celite and the flask and filter cake were rinsed well with ~1 l of 3:1 v/v water/acetic acid. The filtrate was concentrated in vacuo to about 50 ml of volume. 300 ml of toluene was added and the mixture concentrated to afford a solid. The solid was suspended in 1:1 v/v methanol/ether, filtered and dried to afford 1.99 g (100%) of the title compound. $^1$H NMR (400 MHz, D$_2$O+NaOD) δ3.97 (1H, s), 6.77 (2H, app t, J=8.8 Hz), 7.01 (2H, app t, J=5.6 Hz).

Via Resolution

Step A' (4-Fluorophenyl)acetyl chloride

A solution of 150 g (0.974 mol) of 4-(fluorophenyl)acetic acid and 1 ml of N,N-dimethylformamide in 500 ml of toluene at 40° C. was treated with 20 ml of thionyl chloride and heated to 40° C. An additional 61.2 ml of thionyl chloride was added dropwise over 1.5 hours. After the addition, the solution was heated at 50° C. for 1 hour, the solvent was removed in vacuo and the residual oil was distilled at reduced pressure (1.5 mmHg) to afford 150.4 g (89.5%) of the title compound, bp=68–70° C.

Step B': Methyl 2-bromo-3-(4-fluorophenyl)acetate

A mixture of 150.4 g (0.872 mol) of 4-(fluorophenyl) acetyl chloride (from Step A') and 174.5 g (1.09 mol) of bromine was irradiated at 40–50° C. with a quartz lamp for 5 hours. The reaction mixture was added dropwise to 400 ml of methanol and the solution was stirred for 16 hours. The solvent was removed in vacuo and the residual oil was distilled at reduced pressure (1.5 mmHg) to afford 198.5 g (92%) of the title compound, bp=106–110° C.

Step C': Methyl (±)-(4fluorophenyl)glycine

A solution of 24.7 g (0.1 mol) of methyl 2-bromo-2-(4-fluorophenyl)acetate (from Step B') and 2.28 g (0.01 mol) of benzyl triethylammonium chloride in 25 ml of methanol was treated with 6.8 g (0.105 mol) of sodium azide and the resulting mixture was stirred for 20 hours at room temperature. The reaction mixture was filtered; the filtrate was diluted with 50 ml of methanol and hydrogenated in the presence of 0.5 g of 10% Pd/C at 50 psi for 1 hour. The solution was filtered and the solvent removed in vacuo. The residue was partitioned between 10% aqueous sodium carbonate solution and ethyl acetate. The organic phase was washed with water, saturated aqueous sodium chloride solution dried over magnesium sulfate and concentrated in vacuo to afford 9.8 g of the title compound as an oil.

Step D': Methyl (S)-(4-fluorophenyl)glycinate

A solution of 58.4 g of methyl (±) 4-(fluorophenyl) glycinate (from Step C') in 110 ml of 7:1 v/v ethanol/water was mixed with a solution of 28.6 g (0.0799 mol) of O,O'-(+)-dibenzoyltartaric acid ((+)-DBT) (28.6 g, 0.0799 mol) in 110 ml of 7:1 v/v ethanol:water and the resulting solution was allowed to age at room temperature. Ethyl acetate (220 ml) was added after crystallisation was complete and the resulting mixture was cooled to −20° C. and filtered to afford 32.4 g of methyl (S)-(4-fluorophenyl) glycinate, (+)-DBT salt (ee=93.2%). The mother liquors were concentrated in vacuo and the free base was liberated by partitioning between ethyl acetate and aqueous sodium carbonate solution. A solution of free base, so obtained, in 110 ml of 7:1 v/v ethanol/water was mixed with a solution of 28.6 g (0.0799 mol) of O,O'-(−)-dibenzoyltartaric acid ((−)-DBT) (28.6 g, 0.0799 mol) in 110 ml of 7:1 v/v ethanol:water and the resulting solution was allowed to age at room temperature. Ethyl acetate (220 ml) was added after crysallisation was complete and the resulting mixture was cooled to −20° C and filtered to afford 47.0 g of methyl (R)-(4-fluorophenyl)glycinate, (−)-DBT salt (ee=75.8%). Recycling of the mother liquors and addition of (+)-DBT gave a second crop of 7.4 g of (S)-(4-fluorophenyl)glycinate, (+)-DBT salt (ee=96.4%). The two crops of the (S)-amino ester (39.8 g) were combined in 200 ml of 7:1 v/v ethanol/water, heated for 30 minutes and cooled to room temperature. Addition of ethyl acetate, cooling, and filtration afforded 31.7 g of (S)-(4-fluorophenyl)glycinate, (+)-DBT salt (ee>98%). Enantiomeric excess was determined by chiral HPLC (Crownpak CR(+) 5% MeOH in aq HClO$_4$ pH2 1.5 ml/min 40° C. 200 nm).

A mixture of 17.5 g of (S)-(4-fluorophenyl)glycinate, (+)-DBT salt and 32 ml of 5.5N HCl (32 ml) was heated at reflux for 1.5 hours. The reaction mixture was concentrated in vacuo and the residue was dissolved in 40 ml of water. The aqueous solution was washed (3×30 ml of ethyl acetate) and the layers were separated. The pH of the aqueous layer was adjusted to 7 using ammonium hydroxide and the precipitated solid was filtered to afford 7.4 g of the title compound (ee=98.8%).

Description 2

4-Benzyl-3-(S)-(4-fluorophenyl)-2-morpholinone

Step A: N-Benzyl-(S)-(4-fluorophenyl)glycine

A solution of 1.87 g (11.05 mmol) of (S)-(4-fluorophenyl)-glycine (from Description 1) and 1.12 ml (11.1 mmol) of benzaldehyde in 11.1 ml of 1N aqueous sodium hydroxide solution and 11 ml of methanol at 0° C. was treated with 165 mg (4.4 mmol) of sodium borohydride. The cooling bath was removed and the resulting mixture was stirred at room temperature for 30 minutes. Second portions of benzaldehyde (1.12 ml (11.1 mmol)) and sodium borohydride (165 mg (4.4 mmol)) were added to the reaction mixture and stirring was continued for 1.5 hours. The reaction mixture was partitioned between 100 ml of ether and 50 ml of water and the layers were separated. The aqueous layer was separated and filtered to remove a small amount if insoluble material. The filtrate was acidified to pH 5 with 2N aqueous hydrochloric acid solution and the solid that had precipitated was filtered, rinsed well with water, then ether, and dried to afford 1.95 g of the title compound. $^1$H NMR (400 MHz, D$_2$O+NaOD) δ3.33 (2H, AB q, J=8.4 Hz), 3.85 (1H, s), 6.79–7.16 (4H, m).

Step B: 4-Benzyl-3-(S)-(4-fluorophenyl)-2-morpholinone

A mixture of 1.95 g (7.5 mmol) of N-benzyl (S)-(4-fluorophenyl)glycine, 3.90 ml (22.5 mmol) of N,N-diisopropyl-ethylamine, 6.50 ml (75.0 mmol) of 1,2-dibromoethane and 40 ml of N,N-dimethylformamide was stirred at 100° C. for 20 hours (dissolution of all solids occurred on warming). The reaction mixture was cooled and concentrated in vacuo. The residue was partitioned between 250 ml of ether and 100 ml of 0.5N potassium hydrogen sulfate solution and the layers were separated. The organic layer was washed with 100 ml of saturated aqueous sodium bicarbonate solution, 3×150 ml of water, dried over magnesium sulfate, and concentrated in vacuo. Flash chromatography on 125 g of silica gel using 3:1 v/v hexanes/ether as the eluant afforded 1.58 g (74%) of the title compound as an oil. $^1$H NMR (400 MHz, CDCl$_3$) δ2.65 (1H, dt, J=3.2, 12.8 Hz), 3.00 (1H, dt, J=12.8, 2.8 Hz), 3.16 (1H, d, J=13.6 Hz), 3.76 (1H, d, J=13.6 Hz), 4.24 (1H, s), 4.37 (1H, dt, J=13.2, 3.2 Hz), 4.54 (1H, dt, J=2.8, 13.2 Hz), 7.07–7.56 (9H, m).

Description 3

4-Benzyl-2-(R)-(3,5-bis(trifluoromethyl) benzoyloxy)-3-(S-(4-fluorophenyl)morpholine A solution of 2.67 g (10.0 mmol) of 4-benzyl-3-(S)-(4-fluorophenyl)-2-morpholinone (Description 2) in 40 ml of dry THF was cooled to −78° C. The cold solution was treated with 12.5 ml of 1.0M L-Selectride® solution in THF, maintaining the internal reaction temperature below −70° C. The resulting solution was stirred cold for 45 minutes and the reaction was charged with 3.60 ml (20.0 mmol) of 3,5-bis(trifluoromethyl)benzoyl chloride. The resulting yellow mixture was stirred cold for 30 minutes and the reaction was quenched with 50 ml of saturated aqueous sodium bicarbonate solution. The quenched mixture was partitioned between 300 ml of ether and 50 ml of water and the layers were separated. The organic layer was dried over magnesium sulfate. The aqueous layer was extracted with 300 ml of ether; the extract was dried and combined with the original organic layer. The combined organics were concentrated in vacuo. Flash chromatography on 150 g of silica gel using 37:3 v/v hexanes/ether as the eluant afforded 4.06 g (80%) of the title compound as a solid. $^1$H NMR (200 MHz, CDCl$_3$) δ2.50 (1H, dt, J=3.4, 12.0 Hz), 2.97 (1H, app d, J=12.0 Hz), 2.99 (1H, d, J=13.6 Hz), 3.72–3.79 (1H, m), 3.82 (1H, d, J=2.6 Hz), 4.00 (1H, d, J=13.6 Hz), 4.20 (dt, J=2.4, 11.6 Hz), 6.22 (1H, d, J=2.6 Hz), 7.22–7.37 (7H, m), 7.57 (2H, app d, J=6.8 Hz), 8.07 (1H, s), 8.47 (2H, s).

Analysis Calcd. for $C_{26}H_{20}F_7NO_3$: C, 59.21; H, 3.82; N, 2.66; F, 25.21. Found: C, 59.06; H, 4.05; N, 2.50; F, 25.18%.

Description 4

4-Benzyl-2-(R)-(1-(3,5-bis(trifluoromethyl)phenyl) ethenyloxy)-3-(S)-(4-fluorophenyl)morpholine

Step A: Dimethyl titanocene

A solution of 2.49 g (10.0 mmol) of titanocene dichloride in 50 ml of ether in the dark at 0° C. was treated with 17.5 ml of 1.4M methyllithium solution in ether maintaining the internal temperature below 5° C. The resulting yellow/orange mixture was stirred at room temperature for 30 minutes and the reaction was quenched by slowly adding 25 g of ice. The quenched reaction mixture was diluted with 50 ml of ether and 25 ml of water and the layers were separated. The organic layer was dried over magnesium sulfate and concentrated in vacuo to afford 2.03 g (98%) of the title compound as a light-sensitive solid. The dimethyl titanocene could be stored as a solution in toluene at 0° C. for at least 2 weeks without apparent chemical degradation. $^1$H NMR (200 MHz, CDCl$_3$) δ−0.15 (6H, s), 6.06 (10H, s).

Step B: 4-Benzyl-2-(R)-(1-(3,5-bis(trifluoromethyl) phenyl)ethenyloxy)-3-(S)-(4-fluorophenyl) morpholine A solution of the compound of Description 3 (2.50 g, 4.9 mmol) and 2.50 g (12.0 mmol) of dimethyl titanocene (from Step A) in 35 ml of 11 v/v THF/toluene was stirred in an oil bath at 80° C. for 16 hours. The reaction mixture was cooled and concentrated in vacuo. Flash chromatography on 150 g of silica gel using 3:1 v/v hexanes/methylene chloride as the eluant afforded 1.71 g (69%) of the title compound as a solid. An analytical sample was obtained via recrystallisation from isopropanol: $^1$H NMR (400 MHz, CDCl$_3$) δ2.42 (1H, dt, J=3.6, 12.0 Hz), 2.90 (1H, app d, J=12.0 Hz), 2.91 (1H, d, J=13.6 Hz), 3.62–3.66 (1H, m), 3.72 (1H, d, J=2.6 Hz), 3.94 (1H, d, J=13.6 Hz), 4.09 (1H, dt, J=2.4, 12.0 Hz), 4.75 (1H, d, J=3.2 Hz), 4.82 (1H, d, J=3.2 Hz), 5.32 (1H, d, J=2.6 Hz), 7.09 (2H, t, J=8.8 Hz), 7.24–7.33 (5H, m), 7.5–7.62 (2H, m), 7.80 (1H, s), 7.90 (2H, s).

Analysis Calcd. for $C_{27}H_{22}F_7NO_2$: C, 61.72; H, 4.22; N, 2.67; F, 25.31. Found: C, 61.79; H, 4.10; N, 2.65; F, 25.27%.

Description 5

2-(R)-(1-(R)-(3,5-Bis(trifluoromethyl)phenyl) ethoxy)-3-(S)-(4-fluorophenyl) morpholine The compound of Description 4 (4.0 g) was dissolved in ethyl acetate (50 ml) and isopropanol (16 ml). To this solution was added palladium on charcoal (1.5 g) and the mixture was hydrogenated at 40 psi for 36 h. The catalyst was removed by filtration through Celite and the solvents were removed in vacuo. The residue was purified by flash chromatography on silica using 100% ethyl acetate and then 1–10% methanol in ethyl acetate. This afforded isomer A 500 mg (15%) and isomer B 2.6 g (80%) as clear oils—isomer B crystallised on standing. For the title compound: $^1$H NMR (400 MHz, CDCl$_3$) δ1.16 (3H, d, J=6.8 Hz), 1.80 (1H, br s), 3.13 (1H, dd, J=3.2, 12.4 Hz), 3.23 (1H, dt, J=3.6, 12.4 Hz), 3.63 (1H, dd, J=2.4, 11.2 Hz), 4.01 (1H, d, J=2.4 Hz), 4.13 (1H, dt, J=3.2, 12.0 Hz), 4.42 (1H, d, J=2.4 Hz), 4.19 (1H, q, J=6.8 Hz), 7.04–7.09 (2H, m), 7.27–7.40 (4H, m), 7.73 (1H, s): MS (FAB) 438 (M+H, 75%), 180 (100%).

HCl salt formation. To a solution of the free base (0.77 g) in diethyl ether (10 ml) was added 1M-HCl in methanol (1.75 ml). The solution was evaporated to dryness and on addition of diethyl ether crystals formed. The solution was filtered and the residue washed with diethyl ether to give the title compound hydrochloride salt. m.p. 248–250° C.

Analysis Calcd. for $C_{20}H_{18}F_7NO_2 \cdot HCl$: C, 50.70; H, 4.04; N, 2.96; Cl, 7 48; Found: C, 50.46; H, 3.85; N, 3.01; Cl, 7.31%.

EXAMPLE 1

2-(R)-(1-(R)-(3,5-Bis(trifluoromethyl)phenyl) ethoxy)-3-(S)-(4-fluorophenyl-4-(3-(5-oxo-1,2,4-triazolo)methylmorpholine The title compound was prepared in 79% yield from 2-(R)-(1-(R)-(3,5-bis(trifluoromethyl)phenyl)ethoxy)-3-(S)-(4-fluorophenyl)morpholine (from Description 5) and N-methylcarboxy-2-chloroacetamidrazone using a procedure anaolgous to Example 18 in European Patent Specification No. 0 577 394.

$^1$H NMR (CDCl$_3$ +CD$_3$OD, 400 MHz): δ1.48 (3H, d, J=6.8 Hz), 2.52 (1H, app t, J=10.4 Hz), 2.85–2.88 (2H, m), 3.47 (1H, d, J=2.8 Hz), 3.63 (1H d, J=4.4 Hz), 3.70 (1H, dd, J=2.0, 11.6 Hz), 4.24 (1H, app t, J=10.8 Hz), 4.35 (1H, d, J=2.8 Hz), 4.91 (1H, q, J=6.8 Hz), 7.07 (2H, app t, J=8.4 Hz), 7.15 (2H, s), 7.37–7.40 (2H, m), 7.65 (1H, s).

Analysis Calcd. for $C_{23}H_{21}F_7N_4O_3$: C, 51.69; H, 3.96; N, 10.48; F, 24.88; Found: C, 51.74; H, 4.04; N, 10.50; F, 24.59%.

EXAMPLE 2

2-(R)-(1-(R)-(3,5-Bis(trifluoromethyl)phenyl) ethoxy)-4-(5-(dimethylaminomethyl)-1,2,3-triazol-4-yl)methyl-3-(S)-(4-fluorophenyl) morpholine Method A a) 2-(R)-(1-(R)-(3,5-Bis(trifluoromethyl)phenyl) ethoxy-3-(S)-(4-fluorophenyl)-4-propargylmorpholine Propargyl bromide (1.9 ml) was added to a stirred mixture of the compound of Description 5 (5 g) and potassium carbonate (4.76 g) in dry dimethylformamide at 23° C. After 15 min the reaction mixture was diluted with water (250 ml) and extracted with ethyl acetate (3×100 ml). The combined organic phases were washed with brine (1×100 ml) then dried ($K_2CO_3$) and concentrated to leave an oil. This was purified by chromatography on silica using ethyl acetate in hexane (1:9 then 1:4) as eluent afford the title compound as an oil. $^1$H NMR (250 MHZ, CDCl$_3$) δ1.50 (3H, d, J=6.6 Hz), 2.21 (1H, s), 2.84 (1H, d, J=11.1 Hz), 2.97 (1H, td, J=3.2, 11.7 Hz), 3.26 (2H, d, J=1.8 Hz), 3.62 (1H, d, J=2.2 Hz), 3.71 (1H, dd, J=2.3, 11.1 Hz), 4.33 (2H, m), 4.89 (1H, q, J=6.6 Hz) 7.03 (2H, t, J=8.6 Hz), 7.18 (2H, s), 7.38 (2H, br s), 7.63 (1H, s). MS (Cl$^+$) m/z 476 (MH, 100%).

b) 2-(R)-(1-(R)-(3,5-Bis(trifluoromethyl)phenyl) ethoxy)-4-(4-dimethylamino)-4-oxo-but-2-ynyl)-3-(S)-(4-fluorophenyl)morpholine A mixture of N,N-dimethylcarbamoyl chloride (0.195 ml), cuprous iodide (2 mg), bis(triphenylphosphine) palladium (II) chloride (2 mg), triphenylphosphine (3 mg) and the compound described in (a) above (1 g) in triethylamine (4 ml) was heated at 90° C. for 5h in an inert atmosphere. The mixture was cooled to 23° C. and methanol (1 ml) was added and the solvent was removed in vacuo. The residue was partitioned between water and ethyl acetate and the layers were separated. The aqueous phase was extracted with ethyl acetate (2×20 ml). The combined organic phases were washed with water, brine, dried (MgSO$_4$) and concentrated to leave an oil. The residue was purified by chromatography on silica using ethyl acetate in hexane (1:1) then ethyl acetate as eluent to provide the title compound as an oil. $^1$H NMR (250 MHz, CDCl$_3$) δ1.49 (3H, d, J=6.6 Hz), 2.84–3.06 (2H, m), 3.00 (3H, s), 3.17 (3H, s), 3.44 (2H, s), 3.64 (1H, br s), 3.73 (1H, dd, J=2.0, 11.1 Hz), 4.33 (2H, m), 4.88 (1H, q, J=6.6 Hz), 7.03 (2H, t, J=8.7 Hz), 7.17 (2H, s), 7.38 (2H, br s), 7.63 (1H, s). MS (Cl$^+$) m/z 547 (MH, 100%).

c) 2-(R)-(1-(R)-(3,5-Bis(trifluoromethyl)phenyl) ethoxy)-4-(5-N,N-dimethylcarboxamido-1,2,3-triazol-4-yl)methyl-3-(S)-(4-flourophenyl) morpholine A mixture of the compound described in (b) above (1.1 g) and sodium azide (0.65 g) in dimethylsulphoxide (7.5 ml) was heated at 70° C. for 17 h. The mixture was cooled to 23° C. and excess dimethylsulphoxide was removed by distillation in vacuo. The residue was partitioned between brine and ethyl acetate. The layers were separated and the organic layer was washed with brine (2×20 ml) then dried (MgSO$_4$) and concentrated to leave an oil. This was purified by chromatography on silica using ethyl acetate in hexane (1:2 then 1:1) and then ethyl acetate as eluent to provide the title compound as a pale yellow foam. $^1$H NMR (360 MHz, CDCl$_3$) δ1.47 (3H, d, J=6.6 Hz), 2.64 (1H, m), 2.90 (1H, d, J=11.6 Hz), 3.09 (3H, s), 3.34 (3H, s), 3.65 (3H, m), 3.92 (1H, d, J=15.5 Hz), 4.27 (1H, td, J=2.1, 9.5 Hz), 4.35 (1H, d, J=2.6 Hz), 4.89 (1H, q, J=6.6 Hz), 7.01 (2H, t, J=8.7 Hz), 7.16 (2H, s), 7.39 (2H, br s), 7.64 (1H, s). m/z 590 (MH, 100%).

d) 2-(R)-(1-(R)-3,5-Bis(trifluoromethyl)phenyl) ethoxy)-4-(5-(dimethylaminomethyl)-1,2,3-triazol-4-yl)methyl-3-(S)-(4-fluorophenyl) morpholine Lithium aluminium hydride (0.47 ml, 1M in tetrahydrofuran) was added dropwise to a solution of the compound described in (c) above (0.11 g) in dry tetrahydrofuran (1 ml) under an inert atmosphere at 23° C. After 30 min sodium hydroxide (10 drops, 1M) was added followed by water (5 drops). Ethyl acetate (50 ml) was then added and the resulting mixture was filtered through a pad of Hyflo. The filtrate was concentrated in vacuo and the residue was purified by chromatography on silica using ethyl acetate in methanol (9:1 then 4:1) as eluant to provide the title compound as a foam. $^1$H NMR (360 MHz, CDCl$_3$) δ1.44 (3H, d, J=6.6 Hz), 2.25 (6H, s), 2.57 (1H, td, J=3.4, 8.55 Hz), 2.90 (1H, d, J=1.7 Hz), 3.25 (1H, d, J=14.0 Hz), 3.43 (1H, d, J=13.6 Hz), 3.45 (1H, d, J=2.2 Hz), 3.53 (1H, d, J=13.6 Hz), 3.61 (1H, d, J=11.2 Hz), 3.78 (1H, d, J=14.0 Hz), 4.22 (1H, t, J=9.3 Hz), 4.32 (1H, d, J=2.2 Hz), 4.86 (1H, q, J=6.6 Hz), 7.06 (2H, t, J=8.7 Hz), 7.16 (2H, s), 7.48 (2H, br s), 7.63 (1H, s). m/z 576 (MH).

Method B a) 2-(R)-1-(R)-(3,5-Bis(trifluoromethyl)phenyl) ethoxy)-3-(S)-4-fluorophenyl)-4-(4-chlorobut-2-ynyl)morpholine A solution of the product of Description 5 (free base, 5 g) in N,N-dimethylformamide (20 ml) was slowly added to a heated (50° C.) solution of 1,4-dichlorbut-2-yne (2.2 ml) and potassium carbonate (4.8 g) in N,N-dimethylformamide (20 ml). The solution was heated for a further 5 h at 50° C. and then the solvent removed in vacuo. To the residue was added water (400 ml) and the product extracted into ethyl acetate (3×150 ml). The combined organic phase washed with water, saturated brine and dried (MgSO$_4$). The solvent was removed in vacuo and the residue chromatographed on silica gel (eluting with 10% ethyl acetate in petroleum ether bp 60–80° C.) to give the title compound. $^1$H NMR (250 MHz, CDCl$_3$) δ1.41 (3H, d, J=6.6 Hz), 2.80 (1H, app. t, J=10.8 Hz), 2.87 (1H, td, J=3.5 Hz, 11.7 Hz), 3.22 (2H, t, J=1.9 Hz), 3.52 (1H, d, J=2.8 Hz), 3.68 (1H, d, J=1.4 Hz, 11.1 Hz), 4.00 (2H, t, J=1.9 Hz), 4.22–4.32 (2H, m), 4.81 (1H, q, J=6.6 Hz), 6.96 (2H, t, J=8.7 Hz), 7.10 (2H, s), 7.31 (2H, br s), 7.56 (1H, s). m/z (Cl$^+$) 524 (M+H, 100%).

b) N-(4-Azidobut-2-ynyl)-2-(R)-(1-(R)-(3,5-bis (trifluoromethyl)phenyl)ethoxy)-3-(S)-(4-fluorophenyl)morpholine To a solution of 2-(R)-(1-(R)-(3,5-bis(trifluoromethyl) phenyl)ethoxy)-3-(S)-(4-fluorophenyl)-4-(4-chlorobut-2-ynyl)morpholine (4 g) in dimethyl sulphoxide (17 ml) was added sodium azide (0.562 g). The solution was stirred for 20 h and aqueous ammonium chloride and ethyl acetate were added. The organic phase was washed with water (2 times), saturated brine and dried (MgSO$_4$). The solvent was removed in vacuo and the residue chromatographed on silica gel (eluting with 20% ethyl acetate in petroleum ether bp 60–80° C.) to give the title compound. $^1$H NMR (360 MHz, CDCl$_3$) δ1.48 (3H, s, J=6.6 Hz), 2.87 (1H, app t, J=10.2 Hz), 2.98 (1H, td, J=3.6, 11.7 Hz), 3.35 (2H, t, J=1.9 Hz), 3.61 (1H, d, J=2.8 Hz), 3.72 (1H, dq, J=1.4 Hz, 10.0 Hz), 3.92 (2H, t, J=1.9 Hz), 4.30–4.40 (2H, m), 4.89(1H, q, J=6.6 Hz), 7.03 (2H, t, J=8.7 Hz), 7.17 (2H, s), 7.27 (2H, br s), 7.63 (1H, s).

c) 2-(R)-(1-(R)-3,5-Bis(trifluoromethyl)phenyl) ethoxy)-4-(5-(dimethylaminomethyl)-1,2,3-triazol-4-yl)methyl-3-(S)-(4-fluorophenyl) morpholine Dimethylamine (approximately 10 ml) was condensed at −80° C. in a pressure tube and to this was added a solution of N-(4-azidobut-2-ynyl)-2-(R)-(1-(R)-(3,5-bis (trifluoromethyl)phenyl)ethoxy)-3-(S)-(4-fluorophenyl) morpholine (3.2 g) in dioxan (15 ml). The tube was sealed and the solution was heated at 90° C. for 16 h. The solution was evaporated to dryness and the residue chromatographed on silica gel (eluting with 5% methanol in dichloromethane containing 0.25% ammonia (SG. 0.88)) and the fractions containing the desired product were evaporated in vacuo to give the title compound. To a solution of this residue in diethyl ether was added 1M-HCl in methanol. The solution was evaporated to dryness and redissolved in diethyl ether to give crystals of the title compound hydrochloride salt. m.p. 194–198° C., $[\alpha]^{22}D$ +65.0° (c=0.5, $H_2O$).

EXAMPLE 3

2-(R)-(1-(R)-(3,5-Bis(trifluoromethyl)phenyl)ethoxy)-3-(S)-(4-fluorophenyl)-4-(5-(pyrrolidinomethyl)-1,2,3-triazol-4-yl)methylmorpholine The title compound was prepared from the product of Description 5 by a method analogous to that described in Example 2 (Method B). m/z (Cl$^+$) 602 (M+H).

Analysis Calcd. for $C_{28}H_{30}F_7N_5O_2$: C, 55.90; H, 5.03; N, 11.64; Found: C, 55.71; H, 4.86; N, 11.53%.

EXAMPLE 4

4-(5-Azetidinylmethyl-1,2,3-triazol-4-yl)methyl-2-(R)-(1-(R)-(3,5-bis(trifluoromethyl)phenyl)ethoxy-3-(S)-(4-fluorophenyl morpholine This compound was prepared following the method described in Example 2 (Method B) using the compound from Description 5 as starting material. $^1$H NMR (360 MHz, CDCl$_3$) δ1.44 (3H, d, J=6.6 Hz), 2.14 (2H, m), 2.55 (1H, dd, J=3.4, 11.9 Hz), 2.87 (1H, d, J=11.9 Hz), 3.21–3.44 (6H, m), 3.58–3.67 (3H 3.75 (1H, d, J=14.0 Hz), 4.2 (1H, t, J=9.3 Hz), 4.31 (1H, d, J=2.8 Hz), 4.85 (1H, m), 0.06 (2H, t, J=8.7 Hz), 7.16 (1H, s), 7.47 (2H, br s), 7.63 (1H, s).

EXAMPLE 5

2-(R)-(1-(R)-(3,5-Bis(trifluoromethyl)phenyl)ethoxy)-3-(S)-(4-fluorophenyl)-4-(3-(4(?)-monophosphoryl-5-oxo-1H,4H-1,2,4-triazolo)methyl)morpholine, dipotassium salt A solution of 450 mg (0.84 mmol) of 2-(R)-(1-(R)-(3,5-bis(trifluoromethyl)phenyl)ethoxy)-3-(S)-(4-fluorophenyl)-4-(3-(5-oxo-1H,4H-1,2,4-triazolo)methyl)morpholine (Example 1) in 20 ml of THF at 0° C. was treated with 0.84 ml of 1.0 $\underline{M}$ n-butyllithium solution in hexanes. The resulting solution was stirred cold for 5 minutes and was treated with 630 mg (1.17 mmol) of tetrabenzylpyrophosphate in one portion as a solid. The cooling bath was removed and the reaction was stirred at room temperature for 45 minutes. The reaction was quenched with 25 ml of saturated aqueous sodium bicarbonate solution and was extracted with 50 ml of ethyl ether. The organic layer was separated, washed with 25 ml of saturated aqueous sodium bicarbonate solution, 25 ml of 0.5 $\underline{N}$ aqueous potassium hydrogen sulfate solution, 25 ml of saturated aqueous sodium chloride solution, dried over magnesium sulfate and concentrated in vacuo. The crude dibenzyl ester was dissolved in 25 ml of methanol. A solution of 168 mg (1.68 mmol) of potassium bicarbonate was added to the ester solution and the resulting mixture was hydrogenated at 40 psi in the presence of 45 mg of 10% palladium on carbon catalyst for 75 minutes. The catalyst was filtered onto a pad of Celite; the reaction flask and filter cake were rinsed well with methanol (~200 ml), the filtrate was concentrated in vacuo and dried. The residue was partially dissolved in methanol and filtered; the filtrate was concentrated and dried. The resulting solid was recrystallized from isopropanol to afford 280 mg of crude title compound. The solid was partitioned between 40 ml of ethyl ether and 20 ml of water; mixing of the layers resulted in an emulsion. Centrifugation at 2800 rpm for 15 minutes broke the emulsion; the aqueous layer was separated and lyophilized to afford 188 mg (33%) of the compound tentatively identified as 2-(R)-(1-(R)-(3,5-bis(trifluoromethyl)phenyl)ethoxy)-3-(S)-(4-fluorophenyl)-4-(3-(4-monophosphoryl-5-oxo-1H-1,2,4-triazolo)methyl)morpholine, dipotassium salt as a solid.

$^1$H NMR (CD$_3$OD, 500 MHz): δ1.43 (3H, d, J=6.5 Hz), 2.45 (1H, app t, J=8.5 Hz), 2.80 (1H, d, J=14.0 Hz), 2.92 (1H, d, J=11.5Hz), 3.47–3.66 (4H, m), 4.25 (1H, app t, J=11.5 Hz), 4.36 (1H, d, J=1.5 Hz), 4.94 (1H, q, J=6.6 Hz), 7.05 (2H, t, J=8.5 Hz), 7.31(2H, s), 7.52 (2H, br s), 7.71 (1H, s).

$^{13}$C NMR (CD$_3$OD, 125 MHz): δ24.7, 52.3, 53.4, 60.5, 70.6, 73.7, 97.2, 116.1 (d, J=21.9), 122.3, 124.6 (q, J=271.0), 127.7, 132,3, 132.6, 132.8, 134.3, 145.2 (d, J=11.0), 147.5, 159.0 (d, J=10.1), 164.0 (d, J=244.4).

The following non-limiting discussion and results illustrate the effects of a combination of an NK-1 receptor antagonist and an opioid analgesic:

NK-1 receptor antagonists have been shown to have broad spectrum anti-emetic actions (see F. D. Tattersall et al, *Neuropharmacol.*, (1994) 33, 259–260) including an anti-emetic action against morphine-induced emesis (see Bountra et al, supra). The analgesic effects of NK-1 receptor antagonists was shown using spinal reflex studies in the decerebrate rabbit model described below, thus CP-99,994 (1–100 μg/kg i.v.) was shown to reduce facilitation of nociceptive spinal reflexes. Morphine, (0.3–1 mg/kg i.v.) had a similar effect in this preparation. When both drugs were given together, in sub-maximal doses, their effects on the nociceptive reflex appeared to be additive, thus showing that the nociceptive effects of the opioid analgesic were surprisingly unaffected by the presence of an NK-1 receptor antagonist.

Methods

Male New Zealand white rabbits (2.5–3.5 kg) were anaesthetised by an injection of 0.9% alphaxalone and 0.3% alphadolone (Saffan) directly into an ear vein. A cervical spinalization was performed and the cerebral cortex removed (decerebration) allowing anaesthesia to be discontinued. The left hind limb was shaved and a bipolar recording electrode inserted into the biceps femoris/semitendinous muscle. A noxious stimulus was applied to the area of the receptive field of the motor units to the skin of the foot. Single shocks (1 ms square pulses; 2 times threshold) were applied at a rate of 1 per minute. The conditioning stimulus was 20 of these impulses at a rate of 1 Hz, producing wind-up. The baseline parameters were again applied 20 seconds following the conditioning stimulus, the first of these stimuli is termed the facilitation of the baseline response. Injections were administered at 15 minute intervals, the first two always being the relevant drug vehicle. The time-course of events throughout the experiment was as shown below:

t=0 mins: Dose with vehicle (i.v.).
t=40 sec: Begin baseline stimulation (1 per minute).
t=10 mins: Conditioning stimulus applied (20 @ 1 Hz; wind-up).
t=10 mins 40 secs: Baseline stimulation resumes (Initial baseline response equates to facilitation).

t=15 mins: Dose with vehicle (i.v.).

t=25 mins: Conditioning stimulus applied.

t=25 mins 40 secs: Baseline stimulation resumes.

t=30 mins: Dose with test compound (i.v.).

t=40 mins: Conditioning stimulus applied.

t=40 mins 40 secs: Baseline stimulation resumes.

t=45 mins and every 15 minutes thereafter: Drug treatment (i.v.).

t=55 mins and every 15 minutes thereafter: Conditioning stimulus applied.

40 seconds after each conditioning stimulus baseline stimulation is resumed.

In each experiment the values obtained to the second vehicle were used as the control response. Each of the values obtained with drug treatment was expressed as a percentage of the control response. In the case of changes in baseline the last four values obtained prior to the conditioning response were taken to represent baseline activity. The effect of drug treatment was determined by comparing the baseline post-drug to the control baseline. Four rabbits were used in each experiment unless otherwise stated.

Results

CP-99,994 produced a dose-dependent reduction in all three measures: baseline, facilitation and wind-up (FIG. 1). Similarly, morphine (FIG. 2) inhibited all parameters. Administration of morphine (0.5 mg/kg, i.v.) prior to performing a dose response curve with CP-99,994 failed to attenuate the CP-99,994 induced inhibition of each measure (FIG. 3). Finally, the inactive enantiomer of CP-99,994, CP-100,263 did not inhibit baseline, facilitation or wind-up responses (FIG. 4). $ID_{50}$ values for all experiments are shown in Table 1, below:

TABLE 1

Effects of CP-99, 994, CP-100, 263, morphine and combination treatment on the inhibition of baseline firing rate, facilitation and wind-up in the decerebrate, spinalized rabbit preparation

| Drug | Baseline ($\mu$g/kg) | Approximate $ID_{50}$ Facilitation ($\mu$g/kg) | Wind-up ($\mu$g/kg) |
|---|---|---|---|
| CP-99, 994 | 50 | 8 | 10 |
| Morphine | 500 | 500 | 500 |
| CP-99, 994 + Morphine (0.5 mg/kg) | <1 | <1 | ~50 |
| CP-100, 263 | >1000 | >1000 | >1000 |

Conclusions $NK_1$ receptor antagonists such as CP-99,994 attenuate the emetic response to morphine in ferrets. In contrast, the anti-nociceptive effects of morphine were not antagonised by CP-99,994 which also had antinociceptive actions. These appeared to be additive to those of morphine in the spinalised decerebrate rabbit preparation. The lack of effect of CP-100,263 (the inactive enantiomer of CP-99,994) indicates that the effects of CP-99,994 are probably due to an action at $NK_1$ receptors rather than through its ion channel activity.

The following examples illustrate pharmaceutical compositions according to the invention.

These formulations may be prepared with separate active ingredients or with with a combination of active ingredients in one composition. In such combined preparations, the ratio of tachykinin antagonist to opioid analgesic will depend upon the choice of active ingredients.

EXAMPLE 6A

Tablets Containing 1–25 mg of Compound

| | Amount mg | | |
|---|---|---|---|
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 6B

Tablets Containing 26–100 mg of Compound

| | Amount mg | | |
|---|---|---|---|
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s) cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50.0 mg and 100 mg of the active compound per tablet.

EXAMPLE 7

Parenteral Injection

| | Amount |
|---|---|
| Active Ingredient(s) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, citric acid monohydrate and sodium chloride are dissolved in a portion of the water. The active ingredient(s) is (are) dissolved or suspended in the solution and made up to volume.

EXAMPLE 8

Topical Formulation

| | Amount |
|---|---|
| Active Ingredient(s) | 1–10 g |
| Emuisifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

Example 9A
(Surface-Active Agent) Injection Formulation

| Active Ingredient(s) | up to 10 mg/kg |
|---|---|
| Tween 80 ™ | up to 2.5% |
| [in 5% aqueous mannitol (isotonic)] | |

The active ingredient(s) is (are) dissolved directly in a solution of the commercially available Tween 80™ (polyoxyethylenesorbitan monooleate) and 5% aqueous mannitol (isotonic).

EXAMPLE 9B
(Emulsion) Injection Formulation

| Active Ingredient(s) | up to 30 mg/ml |
|---|---|
| Intralipid ™ (10–20%) | |

The active ingredient(s) is (are) dissolved directly in the commercially available Intralipid™ (10 or 20%) to form an emulsion.

EXAMPLE 9C
Alternative (Emulsion) Injectable Formulation

| | Amount |
|---|---|
| Active Ingredient(s) | 0.1–10 mg |
| Soybean oil | 100 mg |
| Egg Phospholipid | 6 mg |
| Glycerol | 22 mg |
| Water for injection | to 1 ml |

All materials are sterilized and pyrogen free. The active ingredient(s) is (are) dissolved in soybean oil. An emulsion is then formed by mixing this solution with the egg phospholipid, glycerol and water. The emulsion is then sealed in sterile vials.

What is claimed is:

1. A method for the treatment or prevention of pain or nociception in a patient in need thereof which comprises administering to the patient an effective amount of a tachykinin antagonist and an opioid analgesic wherein the tachykinin antagonist is a compound of formula (I):

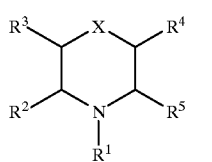

or a pharmaceutically acceptable salt thereof, wherein:
$R^1$ is selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl-$C_{1-3}$alkoxy,
(e) phenyl,
(f) —CN,
(g) halo,
(h) —$NR^9R^{10}$, wherein $R^9$ and $R^{10}$ are independently selected from:
(i) hydrogen,
(ii) $C_{1-6}$alkyl,
(iii) hydroxy-$C_{1-6}$alkyl, and
(iv) phenyl,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above,
(n) heterocycle, wherein the heterocycle is selected from the group consisting of:
(A) benzimidazolyl,
(B) benzofuranyl,
(C) benzthiophenyl,
(D) benzoxazolyl,
(E) furanyl,
(F) imidazolyl,
(G) indolyl,
(H) isoxazolyl,
(I) isothiazolyl,
(J) oxadiazolyl,
(K) oxazolyl,
(L) pyrazinyl,
(M) pyrazolyl,
(N) pyridyl,
(O) pyrimidyl,
(P) pyrrolyl,
(Q) quinolyl,
(R) tetrazolyl,
(S) thiadiazolyl,
(T) thiazolyl,
(U) thienyl,
(V) triazolyl,
(W) azetidinyl,
(X) 1,4-dioxanyl,
(Y) hexahydroazepinyl,
(Z) oxanyl,
(AA) piperazinyl,
(AB) piperidinyl,
(AC) pyrrolidinyl,
(AD) tetrahydrofuranyl, and
(AE) tetrahydrothienyl,
and wherein the heterocylcle is unsubstituted or substituted with one or more substituent(s) selected from:
(i) $C_{1-6}$alkyl, unsubstituted or substituted with halo, —$CF_3$, —$OCH_3$, or phenyl,
(ii) $C_{1-6}$alkoxy,
(iii) oxo,
(iv) hydroxy,
(v) thioxo,
(vi) —$SR^9$, wherein $R^9$ is as defined above,
(vii) halo,
(viii) cyano,
(ix) phenyl,
(x) trifluoromethyl,
(xi) —$(CH_2)_m$—$NR^9R^{10}$, wherein m is 0, 1 or 2, and $R^9$ and $R^{10}$ are as defined above,
(xii) —$NR^9COR^{10}$, wherein $R^9$ and $R^{10}$ are as defined above, (xiii) —CONR$^9$R$^{10}$, wherein R$^9$ and R$^{10}$ are as defined above,
(xiv) —CO$_2$R$^9$, wherein R$^9$ is as defined above, and
(xv) —(CH$_2$)$_m$—OR$^9$, wherein m and R$^9$ are as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —CONR$^9$R$^{10}$, wherein R$^9$ and R$^{10}$ are as defined above,
(i) —COR$^9$, wherein R$^9$ is as defined above,
(k) —CO$_2$R$^9$, wherein R$^9$ is as defined above,
(k) heterocycle, wherein the heterocycle is as defined above;
(4) C$_{2-6}$alkynyl;
(5) phenyl, unsubstitued or substituted with one or more of the substituent(s) selected from:
(a) hydroxy,
(b) C$_{1-6}$alkoxy,
(c) C$_{1-6}$alkyl,
(d) C$_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —C$_2$R$^9$, wherein R$^9$ is as defined above;

R$^2$ and R$^3$ are independently selected from the group consisting of:
(1) hydrogen;
(2) C$_{1-6}$alkyl, unsubstituted or substituted with one or more of the substituents selected from:
(a) hydroxy,
(b) oxo,
(c) C$_{1-6}$alkoxy,
(d) phenyl-C$_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —C(2 R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl—C$_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$, wherein R$^9$ is as defined above,
(l) —CO$_2$R$^9$, wherein R$^9$ is as defined above;
(4) C$_{2-6}$alkynyl;
(5) phenyl, unsubstituted or substituted with one or more of the substituent(s) selected from:
(a) hydroxy,
(b) C$_{1-6}$alkoxy,
(c) C$_{1-6}$alkyl,
(d) C$_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above,
(o) —CO$_2$R$^9$, wherein R$^9$ is as defined above;

and the groups R$^1$ and R$^2$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) oxazolyl, and
(g) thiazolyl,
and wherein the heterocyclic ring is unsubstituted or substituted with one or more substituent(s) selected from:
(i) C$_{1-6}$alkyl,
(ii) oxo,
(iii) C$_{1-b\ 6}$alkoxy,
(iv) —NR$^9$R$^{10}$, wherein R$^9$ and R$^{10}$ are as defined above,
(v) halo, and
(vi) trifluoromethyl;
and the groups R$^2$ and R$^3$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) C$_{1-6}$alkyl,
(ii) C$_{1-6}$alkoxy,
(iii) —NR$^9$R$^{10}$, wherein R$^9$ and R$^{10}$ are as defined above, (iv) halo, and
(v) trifluoromethyl;
and the groups $R^2$ and $R^3$ may be joined together to form a heterocyclic ring selected from the group consisting of:
(a) pyrrolidinyl,
(b) piperidinyl,
(c) phenyl,
(d) pyridinyl,
(e) imidazolyl,
(f) furanyl,
(g) oxazolyl,
(h) thienyl, and
(i) thiazolyl,
and wherein the carbocyclic ring is unsubstituted or substituted with one or more substituent selected from:
(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;
X is selected from the group consisting of:
(1) —O—,
(2) —S—,
(3) —SO—, and
(4) —$SO_2$—;
$R^4$ is selected from the group consisting of:
(1)

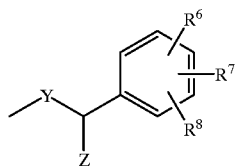

(2) —Y—$C_{1-8}$alkyl, wherein alkyl is unsubstituted or substituted with one or more of the substituents selected from:
(a) hydroxy,
(b) oxo,
(c) $C_{1-6}$alkoxy,
(d) phenyl—$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;
(3) —Y—$C_{2-6}$alkenyl, wherein the alkenyl is unsubstituted or substituted with one or more of the substituent(s) selected from:
(a) hydroxy,
(b) oxo,
(c) $C_{1-6}$alkoxy,
(d) phenyl—$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above,
(4) —O(CO)—phenyl, wherein the phenyl is unsubstituted or substituted with one or more of $R^6$, $R^7$ and $R^8$;
$R^5$ is selected from the group consisting of:
(1) phenyl, unsubstituted or substituted with one or more of $R^{11}$, $R^{12}$ and $R^{13}$;
(2) $C_{1-8}$alkyl, unsubstituted or substituted with one or more of the substituent(s) selected from:
(a) hydroxy,
(b) oxo,
(c) $C_{1-6}$alkoxy,
(d) phenyl—$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above,
(m) —$CO_2R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl—$C_{1-3}$alkoxy,
(e) phenyl,
(f) —CN,
(g) halo,
(h) —$CONR^9R^{10}$, wherein $R^9$ and $R^{10}$ are as defined above,
(i) —$COR^9$, wherein $R^9$ is as defined above,
(j) —$CO_2R^9$, wherein $R^9$ is as defined above;
(4) heterocycle, wherein the heterocycle is as defined above;
$R^6$, $R^7$ and $R^8$ are independently selected from the group consisting of:
(1) hydrogen;
(2) $C_{1-6}$alkyl, unsubstituted or substituted with one or more of the substituents selected from:
(a) hydroxy,
(b) oxo,
(c) $C_{1-6}$alkoxy,
(d) phenyl—$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above, and
(m) —$CO_2R^9$, wherein $R^9$ is as defined above;

(3) $C_{2-6}$alkenyl, unsubstituted or substituted with one or more of the substituent(s) selected from:
  (a) hydroxy,
  (b) oxo,
  (c) $C_{1-6}$alkoxy,
  (d) phenyl—$C_{1-3}$alkoxy,
  (e) phenyl,
  (f) —CN,
  (g) halo,
  (h) —$CONR^9R^{10}$ wherein $R^9$ and $R^{10}$ are as defined above,
  (i) —$COR^9$ wherein $R^9$ is as defined above,
  (j) —$CO_2R^9$, wherein $R^9$ is as defined above;
(4) $C_{2-6}$alkynyl;
(5) phenyl, unsubstituted or substituted with one or more of the substituent(s) selected from:
  (a) hydroxy,
  (b) $C_{1-6}$alkoxy,
  (c) $C_{1-6}$alkyl,
  (d) $C_{2-5}$alkenyl,
  (e) halo,
  (f) —CN,
  (g) —$NO_2$,
  (h) —$CF_3$,
  (i) —$(CH_2)_m$—$NR^9R^{10}$, wherein m, $R^9$ and $R^{10}$ are as defined above,
  (j) —$NR^9COR^{10}$, wherein $R^9$ and $R^{10}$ are as defined above,
  (k) —$NR^9CO_2R^{10}$, wherein $R^9$ and $R^{10}$ are as defined above,
  (l) —$CONR^9R^{10}$, wherein $R^9$ and $R^{10}$ are as defined above,
  (m) —$CO_2NR^9R^{10}$, wherein $R^9$ and $R^{10}$ are as defined above,
  (n) —$COR^9$, wherein $R^9$ is as defined above;
  (o) —$CO_2R^9$, wherein $R^9$ is as defined above;
(6) halo,
(7) —CN,
(8) —$CF_3$,
(9) —$NO_2$,
(10) —$SR^{14}$, wherein $R^{14}$ is hydrogen or $C_{1-5}$alkyl,
(11) —$SOR^{14}$, wherein $R^{14}$ is as defined above,
(12) —$SO_2R^{14}$, wherein $R^{14}$ is as defined above,
(13) $NR^9COR^{10}$, wherein $R^9$ and $R^{10}$ are as defined above,
(14) $CONR^9COR^{10}$, wherein $R^9$ and $R^{10}$ are as defined above,
(15) $NR^9R^{10}$, wherein $R^9$ and $R^{10}$ are as defined above,
(16) $NR^9CO_2R^{10}$, wherein $R^9$ and $R^{10}$ are as defined above,
(17) hydroxy,
(18) $C_{1-6}$alkoxy,
(19) $COR^9$, wherein $R^9$ is as defined above,
(20) $CO_2R^9$, wherein $R^9$ is as defined above,
$R^{11}$, $R^{12}$ and $R^{13}$ are independently selected from the definitions of $R^6$, $R^7$ and $R^8$;
Y is selected from the group consisting of:
(1) a single bond,
(2) —O—,
(3) —S—,
(4) —CO—,
(5) —$CH_2$—,
(6) —$CHR^{15}$—, and
(7) —$CR^{15}R^{16}$—, wherein $R^{15}$ and $R^{16}$ are independently selected from the group consisting of:
  (a) $C_{1-6}$alkyl, unsubstituted or substituted with one or more of the substituents selected from:
    (i) hydroxy,
    (ii) oxo,
    (iii) $C_{1-6}$alkoxy,
    (iv) phenyl—$C_{1-3}$alkoxy,
    (v) phenyl,
    (vi) —CN,
    (vii) halo,
    (viii) —$NR^9R^{10}$, wherein $R^9$ and $R^{10}$ are as defined above,
    (ix) —$NR^9COR^{10}$, wherein $R^9$ and $R^{10}$ are as defined above,
    (x) —$NR^9CO_2R^{10}$, wherein $R^9$ and $R^{10}$ are as defined above,
    (xi) —$CONR^9R^{10}$, wherein $R^9$ and $R^{10}$ are as defined above,
    (xii) —$COR^9$, wherein $R^9$ is as defined above, and
    (xiii) —$CO_2R^9$, wherein $R^9$ is as defined above;
  (b) phenyl, unsubstituted or substituted with one or more of the substituent(s) selected from:
    (i) hydroxy,
    (ii) $C_{1-6}$alkoxy,
    (iii) $C_{1-6}$alkyl,
    (iv) $C_{2-5}$alkenyl,
    (v) halo,
    (vi) —CN,
    (vii) —$NO_2$,
    (viii) —$CF_3$,
    (ix) —$(CH_2)_m$—$NR^9R^{10}$, wherein m, $R^9$ and $R^{10}$ are as defined above,
    (x) —$NR^9COR^{10}$, wherein $R^9$ and $R^{10}$ are as defined above,
    (xi) —$NR^9CO_2R^{10}$, wherein $R^9$ and $R^{10}$ are as defined above,
    (xii) —$CONR^9R^{10}$, wherein $R^9$ and $R^{10}$ are as defined above,
    (xiii) —$CO_2NR^9R^{10}$, wherein $R^9$ and $R^{10}$ are as defined above,
    (xiv) —$COR^9$, wherein $R^9$ is as defined above, and
    (xv) —$CO_2R^9$, wherein $R^9$ is as defined above;
Z is selected from:
(1) hydrogen,
(2) $C_{1-4}$alkyl, and
(3) hydroxy, with the proviso that if Y is —O—, Z is other than hydroxy, or if Y is —$CHR^{15}$—, then Z and $R^{15}$ may be joined together to form a double bond.

2. The method as claimed in claim 1 wherein the opioid analgesic is selected from morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

3. A pharmaceutical composition comprising a tachykinin antagonist and an opioid analgesic wherein the tachykinin antagonist is a compound of formula (I):

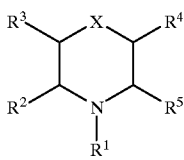

(I)

or a pharmaceutically acceptable salt thereof, wherein:
$R^1$ is selected from the group consisting of:
(1) hydrogen;
(2) $C_{1-6}$alkyl, unsubstituted or substituted with one or more of the substituents selected from:
 (a) hydroxy,
 (b) oxo,
 (c) $C_{1-6}$alkoxy,
 (d) phenyl—$C_{1-3}$alkoxy,
 (e) phenyl,
 (f) —CN,
 (g) halo,
 (h) —$NR^9R^{10}$, wherein $R^9$ and $R^{10}$ are independently selected from:
  (i) hydrogen,
  (ii) $C_{1-6}$alkyl,
  (iii) hydroxy—$C_{1-6}$alkyl, and
  (iv) phenyl,
 (i) —$NR^9COR^{10}$, wherein $R^9$ and $R^{10}$ are as defined above,
 (j) —$NR^9CO_2R^{10}$, wherein $R^9$ and $R^{10}$ are as defined above,
 (k) —$CONR^9R^{10}$, wherein $R^9$ and $R^{10}$ are as defined above,
 (l) —$COR^9$, wherein $R^9$ is as defined above,
 (m) —$CO_2R^9$, wherein $R^9$ is as defined above,
 (n) heterocycle, wherein the heterocycle is selected from the group consisting of:
  (A) benzimidazolyl,
  (B) benzofuranyl,
  (C) benzthiophenyl,
  (D) benzoxazolyl,
  (E) furanyl,
  (F) imidazolyl,
  (G) indolyl,
  (H) isoxazolyl,
  (I) isothiazolyl,
  (J) oxadiazolyl,
  (K) oxazolyl,
  (L) pyrazinyl,
  (M) pyrazolyl,
  (N) pyridyl,
  (L) pyrimidyl,
  (P) pyrrolyl,
  (Q) quinolyl,
  (R) tetrazolyl,
  (S) thiadiazolyl,
  (T) thiazolyl,
  (U) thienyl,
  (V) triazolyl,
  (W) azetidinyl,
  (X) 1,4-dioxanyl,
  (Y) hexahydroazepinyl,
  (Z) oxanyl,
  (AA) piperazinyl,
  (AB) piperidinyl,
  (AC) pyrrolidinyl,
  (AD) tetrahydrofuranyl, and
  (AE) tetrahydrothienyl,
 and wherein the heterocylcle is unsubstituted or substituted with one or more substituent(s) selected from:
  (i) $C_{1-6}$alkyl, unsubstituted or substituted with halo, —$CF_3$, —$OCH_3$, or phenyl,
  (ii) $C_{1-6}$alkoxy,
  (iii) oxo,
  (iv) hydroxy,
  (v) thioxo,
  (vi) —$SR^9$, wherein $R^9$ is as defined above,
  (vii) halo,
  (viii) cyano,
  (ix) phenyl,
  (x) trifluoromethyl,
  (xi) —$(CH_2)_m$—$NR^9R^{10}$, wherein m is 0, 1 or 2, and $R^9$ and $R^{10}$ are as defined above,
  (xii) —$NR^9COR^{10}$, wherein $R^9$ and $R^{10}$ are as defined above,
  (xiii) —$CONR^9R^{10}$, wherein $R^9$ and $R^{10}$ are as defined above,
  (xiv) —$CO_2R^9$, wherein $R^9$ is as defined above, and
  (xv) —$(CH_2)_m$—$OR^9$, wherein m and $R^9$ are as defined above;
(3) $C_{2-6}$alkenyl, unsubstituted or substituted with one or more of the substituent(s) selected from:
 (a) hydroxy,
 (b) oxo,
 (c) $C_{1-6}$alkoxy,
 (d) phenyl—$C_{1-3}$alkoxy,
 (e) phenyl,
 (f) —CN,
 (g) halo,
 (h) —$CONR^9R^{10}$, wherein $R^9$ and $R^{10}$ are as defined above,
 (i) —$COR^9$, wherein $R^9$ is as defined above,
 (j) —$CO_2R^9$, wherein $R^9$ is as defined above,
 (k) heterocycle, wherein the heterocycle is as defined above;
(4) $C_{2-6}$alkynyl;
(5) phenyl, unsubstitued or substituted with one or more of the substituent(s) selected from:
 (a) hydroxy,
 (b) $C_{1-6}$alkoxy,
 (c) $C_{1-6}$alkyl,
 (d) $C_{2-5}$alkenyl,
 (e) halo,
 (f) —CN,
 (g) —$NO_2$,
 (h) —$CF_3$,
 (i) —$(CH_2)_m$—$NR^9R^{10}$, wherein m, $R^9$ and $R^{10}$ are as defined above,
 (j) —$NR^9COR^{10}$, wherein $R^9$ and $R^{10}$ are as defined above,
 (k) —$NR^9CO_2R^{10}$, wherein $R^9$ and $R^{10}$ are as defined above,
 (l) —$CONR^9R^{10}$, wherein $R^9$ and $R^{10}$ are as defined above,
 (m) —$CO_2NR^9R^{10}$, wherein $R^9$ and $R^{10}$ are as defined above,
 (n) —$COR^9$, wherein $R^9$ is as defined above,
 (o) —$CO_2R^9$, wherein $R^9$ is as defined above;
$R^2$ and $R^3$ are independently selected from the group consisting of:
(1) hydrogen;
(2) $C_{1-6}$alkyl, unsubstituted or substituted with one or more of the substituents selected from:

(a) hydroxy,
(b) oxo,
(c) $C_{1-6}$alkoxy,
(d) phenyl—$C_{1-3}$alkoxy,
(e) phenyl,
(f) —CN,
(g) halo,
(h) —$NR^9R^{10}$, wherein $R^9$ and $R^{10}$ are as defined above,
(i) —$NR^9COR^{10}$, wherein $R^9$ and $R^{10}$ are as defined above,
(j) —$NR^9CO_2R^{10}$, wherein $R^9$ and $R^{10}$ are as defined above,
(k) —$CONR^9R^{10}$, wherein $R^9$ and $R^{10}$ are as defined above,
(l) —$COR^9$, wherein $R^9$ is as defined above, and
(m) —$CO_2R^9$, wherein $R^9$ is as defined above;
(3) $C_{2-6}$alkenyl, unsubstituted or substituted with one or more of the substituent(s) selected from:
(a) hydroxy,
(b) oxo,
(c) $C_{1-6}$alkoxy,
(d) phenyl—$C_{1-3}$alkoxy,
(e) phenyl,
(f) —CN,
(g) halo,
(h) —$CONR^9R^{10}$ wherein $R^9$ and $R^{10}$ are as defined above,
(i) —$COR^9$, wherein $R^9$ is as defined above,
(j) —$CO_2R^9$, wherein $R^9$ is as defined above;
(4) $C_{2-6}$alkynyl;
(5) phenyl, unsubstituted or substituted with one or more of the substituent(s) selected from:
(a) hydroxy,
(b) $C_{1-6}$alkoxy,
(c) $C_{1-6}$alkyl,
(d) $C_{2-5}$alkenyl,
(e) halo,
(f) —CN,
(g) —$NO_2$,
(h) —$CF_3$,
(i) —$(CH_2)_m$—$NR^9R^{10}$, wherein m, $R^9$ and $R^{10}$ are as defined above,
(j) —$NR^9COR^{10}$, wherein $R^9$ and $R^{10}$ are as defined above,
(k) —$NR^9CO_2R^{10}$, wherein $R^9$ and $R^{10}$ are as defined above,
(l) —$CONR^9R^{10}$, wherein $R^9$ and $R^{10}$ are as defined above,
(m) —$CO_2NR^9R^{10}$, wherein $R^9$ and $R^{10}$ are as defined above,
(n) —$COR^9$, wherein $R^9$ is as defined above,
(o) —$CO_2R^9$, wherein $R^9$ is as defined above;
and the groups $R^1$ and $R^2$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) oxazolyl, and
(g) thiazolyl,
and wherein the heterocyclic ring is unsubstituted or substituted with one or more substituent(s) selected from:

(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;
and the groups $R^2$ and $R^3$ may be joined together to form a carbocyclic ring selected from the group consisting of:
(a) cyclopentyl,
(b) cyclohexyl,
(c) phenyl,
and wherein the carbocyclic ring is unsubstituted or substituted with one or more substituents selected from:
(i) $C_{1-6}$alkyl,
(ii) $C_{1-6}$alkoxy,
(iii) —$NR^9R^{10}$, wherein $R^9$ and $R^{10}$ are as defined above,
(iv) halo, and
(v) trifluoromethyl;
and the groups $R^2$ and $R^3$ may be joined together to form a heterocyclic ring selected from the group consisting of:
(a) pyrrolidinyl,
(b) piperidinyl,
(c) pyrrolyl,
(d) pyridinyl,
(e) imidazolyl,
(f) furanyl,
(g) oxazolyl,
(h) thienyl, and
(i) thiazolyl,
and wherein the heterocyclic ring is unsubstituted or substituted with one or more substituent(s) selected from:
(i) $C_{1-6}$alkyl,
(ii) oxo,
(iii) $C_{1-6}$alkoxy,
(iv) —$NR^9R^{10}$, wherein $R^9$ and $R^{10}$ are as defined above,
(v) halo, and
(vi) trifluoromethyl;
X is selected from the group consisting of:
(1) —O—,
(2) —S—,
(3) —SO—, and
(4) —$SO_2$—;
$R^4$ is selected from the group consisting of:
(1)

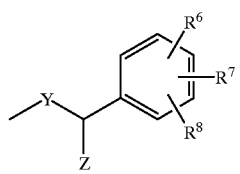

(2) —Y—$C_{1-8}$alkyl, wherein alkyl is unsubstituted or substituted with one or more of the substituents selected from:
(a) hydroxy,
(b) oxo,
(c) $C_{1-6}$alkoxy,
(d) phenyl—$C_{1-3}$alkoxy, (e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above,
(m) —CO$_2$R$^9$, wherein R$^9$ is as defined above;
(3) —Y—C$_{2-6}$alkenyl, wherein the alkenyl is unsubstituted or substituted with one or more of the substituent(s) selected from:
(a) hydroxy,
(b) oxo,
(c) C$_{1-6}$alkoxy,
(d) phenyl—C$_{1-3}$alkoxy,
(e) phenyl,
(f) —CN,
(g) halo,
(h) —CONR$^9$R$^{10}$, wherein R$^9$ and R$^{10}$ are as defined above,
(i) —COR$^9$, wherein R$^9$ is as defined above,
(j) —CO$_2$R$^9$, wherein R$^9$ is as defined above,
(4) —O(CO)—phenyl, wherein the phenyl is unsubstituted or substituted with one or more of R$^6$, R$^7$ and R$^8$;

R$^5$ is selected from the group consisting of:
(1) phenyl, unsubstituted or substituted with one or more of R$^{11}$, R$^{12}$ and R$^{13}$;
(2) C$_{1-8}$alkyl, unsubstituted or substituted with one or more of the substituent(s) selected from:
(a) hydroxy,
(b) oxo,
(c) C$_{1-6}$alkoxy,
(d) phenyl—C$_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$_2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above,
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl—C$_{1-3}$alkoxy,
(e) phenyl,
(f) —CN,
(g) halo,
(h) —CONR$^9$R$^{10}$, wherein R$^9$ and R$^{10}$ are as defined above,
(i) —COR$^9$, wherein R$^9$ is as defined above,
(j) —CO$_2$R$^9$, wherein R$^9$ is as defined above;
(4) heterocycle, wherein the heterocycle is as defined above;

R$^6$, R$^7$ and R$^8$ are independently selected from the group consisting of:
(1) hydrogen;
(2) C$_{1-6}$alkyl, unsubstituted or substituted with one or more of the substituents selected from:
(a) hydroxy,
(b) oxo,
(c) C$_{1-6}$alkoxy,
(d) phenyl—C$_{1-3}$alkoxy,
(e) phenyl,
(f) —CN,
(g) halo,
(h) —NR$^9$R$^{10}$, wherein R$^9$ and R$^{10}$ are as defined above,
(i) —NR$^9$COR$^{10}$, wherein R$^9$ and R$^{10}$ are as defined above,
(j) —NR$^9$CO$^2$R$^{10}$, wherein R$^9$ and R$^{10}$ are as defined above,
(k) —CONR$^9$R$^{10}$, wherein R$^9$ and R$^{10}$ are as defined above,
(l) —COR$^9$, wherein R$^9$ is as defined above, and
(m) —CO$_2$R$^9$, wherein R$^9$ is as defined above;
(3) C$_{2-6}$alkenyl, unsubstituted or substituted with one or more of the substituent(s) selected from:
(a) hydroxy,
(b) oxo,
(c) C$_{1-6}$alkoxy,
(d) phenyl—C$_{1-3}$alkoxy,
(e) phenyl,
(f) —CN,
(g) halo,
(h) —CONR$^9$R$^{10}$ wherein R$^9$ and R$^{10}$ are as defined above,
(i) —COR$^9$ wherein R$^9$ is as defined above,
(j) —CO$_2$R$^9$, wherein R$^9$ is as defined above;
(4) C$_{2-6}$alkynyl;
(5) phenyl, unsubstituted or substituted with one or more of the substituent(s) selected from:
(a) hydroxy,
(b) C$_{1-6}$alkoxy,
(c) C$_{1-6}$alkyl,
(d) C$_{2-5}$alkenyl,
(e) halo,
(f) —CN,
(g) —NO$_2$,
(h) —CF$_3$,
(i) —(CH$_2$)$_m$—NR$^9$R$^{10}$, wherein m, R$^9$ and R$^{10}$ are as defined above,
(j) —NR$^9$COR$^{10}$, wherein R$^9$ and R$^{10}$ are as defined above,
(k) —NR$^9$CO$_2$R$^{10}$, wherein R$^9$ and R$^{10}$ are as defined above,
(l) —CONR$^9$R$^{10}$, wherein R$^9$ and R$^{10}$ are as defined above,
(m) —CO$_2$NR$^9$R$^{10}$, wherein R$^9$ and R$^{10}$ are as defined above,
(n) —COR$^9$, wherein R$^9$ is as defined above;
(o) —CO$_2$R$^9$, wherein R$^9$ is as defined above;
(6) halo,
(7) —CN,
(8) —CF$_3$,
(9) —NO$_2$,
(10) —SR$^{14}$, wherein R$^{14}$ is hydrogen or C$_{1-5}$alkyl,
(11) —SOR$^{14}$, wherein R$^{14}$ is as defined above,
(12) —SO$_2$R$^{14}$, wherein R$^{14}$ is as defined above,
(13) NR$^9$COR$^{10}$, wherein R$^9$ and R$^{10}$ are as defined above,
(14) CONR$^9$COR$^{10}$, wherein R$^9$ and R$^{10}$ are as defined above,

(15) $NR^9R^{10}$, wherein $R^9$ and $R^{10}$ are as defined above,
(16) $NR^9CO_2R^{10}$, wherein $R^9$ and $R^{10}$ are as defined above,
(17) hydroxy,
(18) $C_{1-6}$alkoxy,
(19) $COR^9$, wherein $R^9$ is as defined above,
(20) $CO_2R^9$, wherein $R^9$ is as defined above, $R^{11}$, $R^{12}$ and $R^{13}$ are independently selected from the definitions of $R^6$, $R^7$ and $R^8$;

Y is selected from the group consisting of:
(1) a single bond,
(2) —O—,
(3) —S—,
(4) —CO—,
(5) —$CH_2$—,
(6) —$CHR^{15}$—, and
(7) —$CR^{15}R^{16}$—, wherein $R^{15}$ and $R^{16}$ are independently selected from the group consisting of:
  (a) $C_{1-6}$alkyl, unsubstituted or substituted with one or more of the substituents selected from:
    (i) hydroxy,
    (ii) oxo,
    (iii) $C_{1-6}$alkoxy,
    (iv) phenyl—$C_{1-3}$alkoxy,
    (v) phenyl,
    (vi) —CN,
    (vii) halo,
    (viii) —$NR^9R^{10}$, wherein $R^9$ and $R^{10}$ are as defined above,
    (ix) —$NR^9COR^{10}$, wherein $R^9$ and $R^{10}$ are as defined above,
    (x) —$NR^9CO_2R^{10}$, wherein $R^9$ and $R^{10}$ are as defined above,
    (xi) —$CONR^9R^{10}$, wherein $R^9$ and $R^{10}$ are as defined above,
    (xii) —$COR^9$, wherein $R^9$ is as defined above, and
    (xiii) —$CO_2R^9$, wherein $R^9$ is as defined above;
  (b) phenyl, unsubstituted or substituted with one or more of the substituent(s) selected from:
    (i) hydroxy,
    (ii) $C_{1-6}$alkoxy,
    (iii) $C_{1-6}$alkyl,
    (iv) $C_{2-5}$alkenyl,
    (v) halo,
    (vi) —CN,
    (vii) —$NO_2$,
    (viii) —$CF_3$,
    (ix) —$(CH_2)_m$—$NR^9R^{10}$, wherein m, $R^9$ and $R^{10}$ are as defined above,
    (x) —$NR^9COR^{10}$, wherein $R^9$ and $R^{10}$ are as defined above,
    (xi) —$NR^9CO_2R^{10}$, wherein $R^9$ and $R^{10}$ are as defined above,
    (xii) —$CONR^9R^{10}$, wherein $R^9$ and $R^{10}$ are as defined above,
    (xiii) —$CO_2NR^9R^{10}$, wherein $R^9$ and $R^{10}$ are as defined above,
    (xiv) —$COR^9$, wherein $R^9$ is as defined above, and
    (xv) —$CO_2R^9$, wherein $R^9$ is as defined above;

Z is selected from:
(1) hydrogen,
(2) $C_{1-4}$alkyl, and
(3) hydroxy, with the proviso that if Y is —O—, Z is other than hydroxy, or if Y is —$CHR^{15}$—, then Z and $R^{15}$ may be joined together to form a double bond.

4. The method of claim 3 wherein the opioid analgesic is selected from morphine, codeine, dihydrocodeine, diacetylmorphine, hydrocodone, hydromorphone, levorphanol, oxymorphone, alfentanil, buprenorphine, butorphanol, fentanyl, sufentanyl, meperidine, methadone, nalbuphine, propoxyphene and pentazocine; or a pharmaceutically acceptable salt thereof.

\* \* \* \* \*